United States Patent
Chen

(10) Patent No.: US 7,018,395 B2
(45) Date of Patent: Mar. 28, 2006

(54) PHOTODYNAMIC TREATMENT OF TARGETED CELLS

(75) Inventor: James Chen, Bellevue, WA (US)

(73) Assignee: Light Sciences Corporation, Snoqualmie, WA (US)

( * ) Notice: Subject to any disclaimer, the term of this patent is extended or adjusted under 35 U.S.C. 154(b) by 155 days.

(21) Appl. No.: 10/802,284

(22) Filed: Mar. 16, 2004

(65) Prior Publication Data

US 2004/0215292 A1    Oct. 28, 2004

Related U.S. Application Data

(63) Continuation of application No. 09/905,501, filed on Jul. 13, 2001, now Pat. No. 6,899,723.

(51) Int. Cl.
  *A61N 5/067* (2006.01)
  *A61K 9/127* (2006.01)

(52) U.S. Cl. .................. 607/88; 607/89; 604/21; 424/450

(58) Field of Classification Search ............. 607/88, 607/89, 90–92; 606/2–16; 604/21; 424/178.1, 424/181.1, 182.1, 450
See application file for complete search history.

(56) References Cited

U.S. PATENT DOCUMENTS

| | | | |
|---|---|---|---|
| 2,797,213 A | 6/1957 | Moore | 260/141 |
| 3,046,118 A | 7/1962 | Schmidt | 96/33 |
| 3,046,120 A | 7/1962 | Schmidt | 96/33 |
| 4,337,759 A | 7/1982 | Popovich et al. | 126/438 |
| 4,521,762 A | 6/1985 | Kapral | 340/347 |
| 4,577,636 A | 3/1986 | Spears | 128/654 |
| 4,675,338 A | 6/1987 | Bommer et al. | 514/410 |
| 4,693,556 A | 9/1987 | McCaughan, Jr. | 350/320 |
| 4,693,885 A | 9/1987 | Bommer et al. | 424/2 |
| 4,753,958 A | 6/1988 | Weinstein et al. | 514/410 |
| 4,823,244 A | 4/1989 | Alaybayoglu et al. | 362/194 |
| 4,849,207 A | 7/1989 | Sakata et al. | 424/1.1 |
| 4,861,876 A | 8/1989 | Kessel | 540/145 |

(Continued)

FOREIGN PATENT DOCUMENTS

AU    0720815    6/1987

(Continued)

OTHER PUBLICATIONS

Adilia et al., "Local delivery of photosensitizing drugs in arteries: a novel approach to photodynamic therapy for the prevention of intimal hyperplasia", *Proc. SPIE-INT. Soc. Opt. Eng.*, 2395:402-8 (1995) (Ger. Symp. Laser Angioplasty, 2nd, 1980).

(Continued)

*Primary Examiner*—Roy D. Gibson
(74) *Attorney, Agent, or Firm*—Fish & Richardson P.C.; Stephanie Seidman; Frank J. Miskiel

(57) ABSTRACT

The present invention is drawn to methods for photodynamic therapy (PDT) of a target cell, target tissue or target composition in a mammalian subject, using a therapeutically effective amount of a targeted substance, which is either a targeted photosensitizing agent, or a photosensitizing agent delivery system, or a targeted prodrug. This targeted substance preferably selectively binds to the target cell, target tissue or target composition. Light at a wavelength or waveband corresponding to that which is absorbed by the targeted substance is then administered. The light intensity is relatively low, but a high total fluence is employed to ensure the activation of the targeted photosensitizing agent or targeted prodrug product.

17 Claims, 13 Drawing Sheets

U.S. PATENT DOCUMENTS

| | | | |
|---|---|---|---|
| 4,866,168 A | 9/1989 | Dougherty et al. | 540/145 |
| 4,878,891 A | 11/1989 | Judy et al. | 604/5 |
| 4,932,934 A | 6/1990 | Dougherty et al. | 604/21 |
| 4,957,481 A | 9/1990 | Gatenby | 604/20 |
| 4,997,639 A | 3/1991 | Aizawa et al. | 424/9 |
| 4,998,930 A | 3/1991 | Lundahl | 606/15 |
| 5,002,962 A | 3/1991 | Pandey et al. | 514/410 |
| 5,026,367 A | 6/1991 | Leckrone et al. | 606/7 |
| 5,028,594 A | 7/1991 | Carson | 514/23 |
| 5,041,078 A | 8/1991 | Matthews et al. | 604/4 |
| 5,053,006 A | 10/1991 | Watson | 604/52 |
| 5,055,446 A | 10/1991 | Alexander et al. | 514/2 |
| 5,171,749 A | 12/1992 | Levy et al. | 514/410 |
| 5,190,536 A | 3/1993 | Wood et al. | 606/16 |
| 5,263,925 A | 11/1993 | Gilmore, Jr. et al. | 604/4 |
| 5,283,255 A | 2/1994 | Levy et al. | 514/410 |
| 5,314,905 A | 5/1994 | Pandey et al. | 514/410 |
| 5,330,741 A | 7/1994 | Smith et al. | 424/9 |
| 5,344,434 A | 9/1994 | Talmore | 607/88 |
| 5,368,841 A | 11/1994 | Trauner et al. | 424/9 |
| 5,399,583 A | 3/1995 | Levy et al. | 514/410 |
| 5,404,869 A | 4/1995 | Parkyn, Jr. et al. | 126/699 |
| 5,430,051 A | 7/1995 | Aizawa et al. | 514/410 |
| 5,441,531 A | 8/1995 | Zarate et al. | 607/90 |
| 5,445,608 A | 8/1995 | Chen et al. | 604/20 |
| 5,456,661 A | 10/1995 | Narciso, Jr. | 604/20 |
| 5,474,528 A | 12/1995 | Meserol | 604/20 |
| 5,474,765 A | 12/1995 | Thorpe | 424/178.17 |
| 5,482,698 A | 1/1996 | Griffiths | 424/1.41 |
| 5,484,778 A | 1/1996 | Kenney et al. | 514/63 |
| 5,484,803 A | 1/1996 | Richter | 514/410 |
| 5,494,793 A | 2/1996 | Schindele et al. | 435/6 |
| 5,498,710 A | 3/1996 | Pandey et al. | 540/145 |
| 5,500,009 A | 3/1996 | Mendes et al. | 607/88 |
| 5,514,669 A | 5/1996 | Selman | 514 |
| 5,519,534 A | 5/1996 | Smith et al. | 359/599 |
| 5,534,506 A | 7/1996 | Morgan et al. | 514/185 |
| 5,543,514 A | 8/1996 | Sessler et al. | 540/472 |
| 5,549,660 A | 8/1996 | Mendes et al. | 607/88 |
| 5,556,612 A | 9/1996 | Anderson et al. | 424/59 |
| 5,565,552 A | 10/1996 | Magda et al. | 534/11 |
| 5,567,409 A | 10/1996 | Aizawa et al. | 424/9.363 |
| 5,571,152 A | 11/1996 | Chen et al. | 607/92 |
| 5,576,013 A | 11/1996 | Williams et al. | 424/423 |
| 5,577,492 A | 11/1996 | Parkyn, Jr. et al. | 126/698 |
| 5,577,493 A | 11/1996 | Parkyn, Jr. et al. | 126/699 |
| 5,591,847 A | 1/1997 | Pandey et al. | 540/472 |
| 5,591,855 A | 1/1997 | Hudkins et al. | 546/256 |
| 5,594,136 A | 1/1997 | Sessler et al. | 540/472 |
| 5,613,769 A | 3/1997 | Parkyn, Jr. et al. | 362/338 |
| 5,616,140 A | 4/1997 | Prescott | 606/10 |
| 5,630,996 A | 5/1997 | Reno et al. | 424/1.49 |
| 5,634,711 A | 6/1997 | Kennedy et al. | 362/119 |
| 5,643,334 A | 7/1997 | Eckhouse et al. | 607/88 |
| 5,645,562 A | 7/1997 | Haan et al. | 606/194 |
| 5,655,832 A | 8/1997 | Pelka et al. | 362/296 |
| 5,676,453 A | 10/1997 | Parkyn, Jr. et al. | 362/260 |
| 5,686,113 A | 11/1997 | Speaker et al. | 424/490 |
| 5,698,866 A | 12/1997 | Doiron et al. | 257/99 |
| 5,700,243 A | 12/1997 | Narciso, Jr. | 604/102 |
| 5,702,432 A | 12/1997 | Chen et al. | 607/88 |
| 5,703,896 A | 12/1997 | Pankove et al. | 372/50 |
| 5,705,518 A | 1/1998 | Richter et al. | 514/410 |
| 5,707,401 A | 1/1998 | Talmore | 607/88 |
| 5,709,653 A | 1/1998 | Leone | 604/20 |
| 5,715,837 A | 2/1998 | Chen | 128/899 |
| 5,735,817 A | 4/1998 | Shantha | 604/100 |
| 5,736,563 A | 4/1998 | Richter | 514/410 |
| 5,741,316 A | 4/1998 | Chen et al. | 607/61 |
| 5,746,494 A | 5/1998 | Koeda et al. | 362/32 |
| 5,746,495 A | 5/1998 | Klamm | 362/32 |
| 5,757,557 A | 5/1998 | Medvedev et al. | 359/708 |
| 5,766,222 A | 6/1998 | Petit | 606/234 |
| 5,766,234 A | 6/1998 | Chen et al. | 607/92 |
| 5,769,844 A | 6/1998 | Ghaffari | 606/16 |
| 5,770,619 A | 6/1998 | Richter et al. | 514/410 |
| 5,770,730 A | 6/1998 | Pandey et al. | 540/472 |
| 5,775,339 A | 7/1998 | Woodburn et al. | 128/898 |
| 5,776,175 A | 7/1998 | Eckhouse et al. | 607/100 |
| 5,776,427 A | 7/1998 | Thorpe et al. | 424/1.49 |
| 5,782,896 A | 7/1998 | Chen et al. | 607/88 |
| 5,797,868 A | 8/1998 | Leone | 604/21 |
| 5,798,349 A | 8/1998 | Levy et al. | 514/185 |
| 5,800,478 A | 9/1998 | Chen et al. | 607/88 |
| 5,803,575 A | 9/1998 | Ansems et al. | 362/32 |
| 5,806,955 A | 9/1998 | Parkyn, Jr. et al. | 362/31 |
| 5,807,881 A | 9/1998 | Leong et al. | 514/410 |
| 5,811,248 A | 9/1998 | Ditlow et al. | 435/7.9 |
| 5,814,008 A | 9/1998 | Chen et al. | 604/21 |
| 5,817,048 A | 10/1998 | Lawandy | 604/20 |
| 5,824,080 A | 10/1998 | Lamuraglia | 623/11 |
| 5,824,657 A | 10/1998 | Hill et al. | 514/46 |
| 5,827,186 A | 10/1998 | Chen et al. | 600/407 |
| 5,829,448 A | 11/1998 | Fisher et al. | 128/898 |
| 5,832,931 A | 11/1998 | Wachter et al. | 128/898 |
| 5,835,648 A | 11/1998 | Narciso, Jr. et al. | 385/31 |
| 5,843,143 A | 12/1998 | Whitehurst | 607/88 |
| 5,849,027 A | 12/1998 | Gart et al. | 607/93 |
| 5,851,225 A | 12/1998 | Lawandy | 607/88 |
| 5,855,866 A | 1/1999 | Thorpe et al. | 424/1.49 |
| 5,863,538 A | 1/1999 | Thorpe et al. | 424/136.1 |
| 5,864,035 A | 1/1999 | Pandey et al. | 540/472 |
| 5,865,840 A | 2/1999 | Chen | 607/92 |
| 5,876,427 A | 3/1999 | Chen et al. | 607/88 |
| 5,881,200 A | 3/1999 | Burt | 385/142 |
| 5,882,328 A | 3/1999 | Levy et al. | 604/20 |
| 5,882,779 A | 3/1999 | Lawandy | 428/323 |
| 5,906,579 A | 5/1999 | Vander Salm et al. | 600/424 |
| 5,909,670 A | 6/1999 | Trader et al. | 705/14 |
| 5,912,257 A | 6/1999 | Prasad et al. | 514/356 |
| 5,913,834 A | 6/1999 | Francais | 600/591 |
| 5,913,884 A | 6/1999 | Trauner et al. | 607/88 |
| 5,919,217 A | 7/1999 | Hughes | 607/90 |
| 5,921,244 A | 7/1999 | Chen et al. | 128/897 |
| 5,924,788 A | 7/1999 | Parkyn, Jr. | 362/329 |
| 5,926,320 A | 7/1999 | Parkyn, Jr. et al. | 359/641 |
| 5,929,105 A | 7/1999 | Sternberg et al. | 514/410 |
| 5,942,534 A | 8/1999 | Trauner et al. | 514/410 |
| 5,943,354 A | 8/1999 | Lawandy | 372/39 |
| 5,945,762 A | 8/1999 | Chen et al. | 310/171 |
| 5,952,329 A | 9/1999 | Cincotta et al. | 514/224.5 |
| 5,957,960 A | 9/1999 | Chen et al. | 607/92 |
| 5,961,543 A | 10/1999 | Waldmann | 607/88 |
| 5,976,175 A | 11/1999 | Hirano et al. | 607/89 |
| 5,976,535 A | 11/1999 | Fritzberg et al. | 424/182.1 |
| 5,985,353 A | 11/1999 | Lawton et al. | 427/2.13 |
| 5,989,245 A | 11/1999 | Prescott | 606/14 |
| 5,990,479 A | 11/1999 | Weiss et al. | 250/307 |
| 5,997,569 A | 12/1999 | Chen et al. | 607/88 |
| 5,997,842 A | 12/1999 | Chen | 424/1.29 |
| 5,998,597 A | 12/1999 | Fisher et al. | 536/23.1 |
| 6,013,053 A | 1/2000 | Bower et al. | 604/96 |
| 6,015,897 A | 1/2000 | Theodore et al. | 540/474 |
| 6,021,347 A | 2/2000 | Herbst et al. | 607/2 |
| 6,032,070 A | 2/2000 | Flock et al. | 600/473 |
| 6,036,941 A | 3/2000 | Bottiroli et al. | 424/9.6 |
| 6,048,359 A | 4/2000 | Biel | 607/92 |
| 6,051,230 A | 4/2000 | Thorpe et al. | 424/178.1 |
| 6,058,937 A | 5/2000 | Doiron et al. | 128/898 |
| 6,071,944 A | 6/2000 | Rodgers et al. | 514/408 |
| 6,080,160 A | 6/2000 | Chen et al. | 606/72 |
| 6,083,485 A | 7/2000 | Licha et al. | 424/9.6 |
| 6,090,788 A | 7/2000 | Lurie | 514/23 |
| 6,092,531 A | 7/2000 | Chen et al. | 128/899 |

| | | | | | |
|---|---|---|---|---|---|
| 6,096,066 A | 8/2000 | Chen et al. .................. 607/88 | WO | 93/00005 | 1/1993 |
| 6,100,290 A | 8/2000 | Levy et al. ................. 514/410 | WO | 93/11657 | 6/1993 |
| 6,107,325 A | 8/2000 | Chan et al. ................. 514/410 | WO | 93/13769 | 7/1993 |
| 6,107,466 A | 8/2000 | Hasan et al. ................ 530/351 | WO | 93/24127 | 12/1993 |
| 6,117,862 A | 9/2000 | Margaron et al. ........... 514/185 | WO | 95/32001 | 11/1995 |
| 6,123,923 A | 9/2000 | Unger et al. ................ 424/9.52 | WO | 96/06641 | 3/1996 |
| 6,135,620 A | 10/2000 | Marsh ........................ 362/377 | WO | 97/31582 | 9/1997 |
| 6,138,681 A | 10/2000 | Chen et al. ................. 128/899 | WO | 97/32520 | 9/1997 |
| 6,152,951 A | 11/2000 | Hashimoto et al. .......... 607/92 | WO | 97/32885 | 9/1997 |
| 6,162,242 A | 12/2000 | Peyman ....................... 607/88 | WO | 97/40679 | 11/1997 |
| 6,165,440 A | 12/2000 | Esenaliev .................. 424/1.11 | WO | 97/46262 | 12/1997 |
| 6,183,444 B1 | 2/2001 | Glines et al. ............... 604/187 | WO | 98/06456 | 2/1998 |
| 6,187,030 B1 | 2/2001 | Gart et al. .................... 607/93 | WO | 98/08565 | 3/1998 |
| 6,210,425 B1 | 4/2001 | Chen .......................... 607/88 | WO | 98/14243 | 4/1998 |
| 6,217,869 B1 | 4/2001 | Meyer et al. ............. 424/178.1 | WO | 98/20936 | 5/1998 |
| RE37,180 E | 5/2001 | Mori et al. ................. 514/410 | WO | 98/24371 | 6/1998 |
| 6,238,426 B1 | 5/2001 | Chen .......................... 607/88 | WO | 98/24510 | 6/1998 |
| 6,273,904 B1 | 8/2001 | Chen et al. .................. 607/88 | WO | 98/32491 | 7/1998 |
| 6,281,611 B1 | 8/2001 | Chen et al. ................. 310/171 | WO | 98/32492 | 7/1998 |
| 6,297,228 B1 | 10/2001 | Clark et al. ................. 514/177 | WO | 98/32493 | 7/1998 |
| 6,319,273 B1 | 11/2001 | Chen et al. .................. 607/88 | WO | 98/33251 | 7/1998 |
| 6,331,744 B1 | 12/2001 | Chen et al. ................. 310/171 | WO | 98/46130 | 10/1998 |
| 6,344,050 B1 | 2/2002 | Chen .......................... 607/88 | WO | 98/47541 | 10/1998 |
| 6,416,531 B1 | 7/2002 | Chen .......................... 607/89 | WO | 98/50034 | 11/1998 |
| 6,454,789 B1 | 9/2002 | Chen .......................... 607/88 | WO | 98/50387 | 11/1998 |
| 6,495,585 B1 | 12/2002 | Bellnier et al. ............. 514/410 | WO | 98/52610 | 11/1998 |
| 6,520,669 B1 | 2/2003 | Chen et al. ................. 362/545 | WO | 98/56302 | 12/1998 |
| 6,534,040 B1 | 3/2003 | Pandey et al. ............. 424/9.362 | WO | 99/03503 | 1/1999 |
| 6,554,853 B1 | 4/2003 | Chen .......................... 607/88 | WO | 94/06424 | 3/1999 |
| 6,580,228 B1 | 6/2003 | Chen et al. ............. 315/185 R | WO | 99/18879 | 4/1999 |
| 6,602,274 B1 | 8/2003 | Chen .......................... 607/88 | WO | 99/20346 | 4/1999 |
| 6,624,187 B1 | 9/2003 | Pandey et al. .............. 514/410 | WO | 99/39769 | 8/1999 |
| 6,657,351 B1 | 12/2003 | Chen et al. ................. 310/171 | WO | 99/58149 | 11/1999 |
| 6,890,555 B1 * | 5/2005 | Desai et al. ................. 424/450 | WO | 99/52565 | 12/1999 |
| 6,899,723 B1 | 5/2005 | Chen .......................... 607/88 | WO | 99/66988 | 12/1999 |
| 2001/0022970 A1 | 9/2001 | Dees et al. ............... 424/178.1 | WO | 99/67248 | 12/1999 |
| 2001/0044623 A1 | 11/2001 | Chen ............................ 606/2 | WO | 99/67249 | 12/1999 |
| 2001/0046983 A1 | 11/2001 | Pandey et al. .............. 514/185 | WO | 00/15296 | 3/2000 |
| 2001/0049502 A1 | 12/2001 | Chen ...................... 604/167.06 | WO | 00/27365 | 5/2000 |
| 2002/0010500 A1 | 1/2002 | Chen .......................... 607/89 | WO | 00/29617 | 5/2000 |
| 2002/0033192 A1 | 3/2002 | Lindseu et al. ............. 136/263 | WO | 00/36983 | 6/2000 |
| 2002/0049247 A1 | 4/2002 | Chen .......................... 514/410 | WO | 00/41725 | 7/2000 |
| 2002/0087205 A1 | 7/2002 | Chen .......................... 607/88 | WO | 00/41726 | 7/2000 |
| 2002/0127224 A1 | 9/2002 | Chen ....................... 424/130.1 | WO | 00/41727 | 7/2000 |
| 2002/0127230 A1 | 9/2002 | Chen ....................... 424/178.1 | WO | 00/41768 | 7/2000 |
| 2002/0128303 A1 | 9/2002 | Bellnier et al. ............. 514/410 | WO | 00/61584 A1 | 10/2000 |
| 2002/0198576 A1 | 12/2002 | Chen .......................... 607/88 | WO | 01/03770 | 1/2001 |
| 2003/0018371 A1 | 1/2003 | Chen .......................... 607/88 | WO | 01/05316 | 1/2001 |
| 2003/0030342 A1 | 2/2003 | Chen et al. ................. 310/102 | WO | 01/15694 | 3/2001 |
| 2003/0109813 A1 | 6/2003 | Chen ............................ 60/2 | WO | 01/43825 | 6/2001 |
| 2003/0114434 A1 | 6/2003 | Chen et al. ................. 514/185 | WO | 01/51087 | 7/2001 |
| 2003/0167033 A1 | 9/2003 | Chen et al. ................... 604/20 | WO | 01/74398 A1 | 10/2001 |
| 2003/0208249 A1 | 11/2003 | Chen .......................... 607/88 | WO | 01/78216 | 10/2001 |
| 2004/0029788 A1 * | 2/2004 | Bender et al. ................ 514/9 | WO | 01/78458 | 10/2001 |
| 2004/0044197 A1 | 3/2004 | Pandey et al. .............. 540/140 | WO | 01/98708 | 12/2001 |
| 2004/0044198 A1 | 3/2004 | Pandey et al. .............. 540/145 | WO | 02/17690 | 2/2002 |
| 2004/0215292 A1 | 10/2004 | Chen .......................... 607/88 | WO | 02/098882 A1 | 12/2002 |
| 2004/0229830 A1 | 11/2004 | Tachibana et al. ........... 514/44 | WO | 03/050082 A2 | 6/2003 |
| | | | WO | 03/052793 | 6/2003 |
| FOREIGN PATENT DOCUMENTS | | | WO | 03/061696 | 7/2003 |
| AU | 0674251 | 6/1994 | WO | 2004/002476 A2 | 1/2004 |
| AU | 0694868 | 3/1996 | WO | 2004/005289 A2 | 1/2004 |
| AU | 0708410 | 2/1997 | | | |
| AU | 0713227 | 9/1997 | | | |
| AU | 0721857 | 4/1999 | | | |
| EP | 0 407 122 | 1/1991 | | | |
| EP | 01/75617 | 10/1991 | | | |
| EP | 1 146 046 A2 | 10/2001 | | | |
| GB | 2323284 | 9/1998 | | | |
| JP | 53084998 | 7/1978 | | | |
| JP | 57185220 | 11/1992 | | | |
| WO | 92/00106 | 1/1992 | | | |

OTHER PUBLICATIONS

Anderson et al. "Photodynamic therapy for sarcoma pulmonary metastases: a preclinical toxicity study," *Anticancer Res.* 23:3713-3718 (2003).

Anonymous (1997) http://www.lumacare.com/, 2 pages.

Anonymous (May 1998) "The 1998 Photonics Circle of Excellence Award Winners", *Photonics Spectra*, pp. 95-96.

Barr et al., Normal tissue Damage Following Photodynamic

Therapy: Are There Biological Advantages?, Book: Photodynamic Therapy, Basic Principles and Clinical Applications, Barbara W. Henderson and Thomas J. Dougherty, (Eds.); Marcel Dekker, Inc. New York, pp. 201-216.

Bayer et al., "Raw eggs and cancer therapy", *Science Spectra, 12*:34-41 (1998).

Beems et al., Photosensitizing properties of bacteriochlorophyllin a and bacteriochlorin a, two derivatives of bacteriochlorophyll a, *Photochem. Photobiol.* 46(5): 639-643 (1987).

Bellnier et al., Murine pharmacokinetics and antitumor efficacy of the photodynamic sensitizer 2-[1-hexyloxyethyl]-2-devinyl pyropheophorbide-a, *J. Photochem. Photobiol. B: Biol.* 20: 55-61 (1993).

Birchler et al., "Selective Targeting and Photocoagulation of Ocular Angiogenesis Mediated by a Phage-Derived Human Antibody Fragment", *Nature Biotechnol.,* 17:984-988 (1999).

Blaauwgeers et al., "Polarized Vascular Endothelial Growth Factor Secretion by Human Retinal Pigment Epithelium and Localization of Vascular Endothelial Growth Factor Receptors on the Inner Choriocapillaris", *American Journal of Pathology,* 155(2): 421-428 (1999).

Boulton et al., "VEGF localization in diabetic retinopathy", *Br J Opthalmol,* 82:561-568 (1998).

Brower, V., "Tumor Angiogenesis—New Drugs on the Block", *Nature Biotechnol.,* 17:963-968 (1999).

Casalini et al., "Tumor Pretargeting: Role Of Avidin/Streptavidin On Monoclonal Antibody Internalization", *J. Nuclear Med.,* 38 (9):1378-1381 (1997).

Cattel et al., "The Role of Conjugation Processes and Linking Agents in the Preparation of Molecular/Particulate Conjugates—a Review", *S.T.P. Pharma. Sci.,* 9 (4):307-319 (1999).

Certified English Translation of Japanese Kokai [Unexamined Patent] No. 57-185220, "Anti-Cancer Drug Having Chlorophyll Derivative Effective,".

Certified English Translation of Japanese Patent Application No. Sho51-159879 (Japanese Kokai [Unexamined Patent] No. 53-84998), "Carcinostatic Method,".

Certified English Translation of: Fischer, H. et al., "[On the Bromination of the Esters of Mesoisochlorin e4 and Mesochlorin e6]," *Berischte der Deutschen Chemischen* 75:1778-1795 (1942).

Chen et al., "New Technology for Deep Light distribution in Tissue for Phototherapy", *The Cancer J.,* 8 (2):154-163 (2002).

Chen et al., "New directions in photodynamic therapy," *ICCP-2. 2nd International Conference on Porphyrins and Phthalocyanines,* Jun. 30 Component, 2002; Kyoto, Japan: 78 [abstract S-26].

Chen, J., "Next Generation Light Delivery System for Multi-Treatment Extended Duration Photodynamic Therapy (MED-PDT)", *SPIE-Proceedings Series,* 2972:161-167 (1997).

Ciulla et al., "Changing therapeutic paradigms for exudative age-relted macular degeneration: antiangiogenic agents and photodynamic therapy", *Exp. Opin. Invest. Drugs, 8(12)*: 2173-2182 (1999).

Dartsch, et al., "Photodynamic therapy of vascular stenoses? Response of cultured human smooth muscle cells from non-atherosclerotic arteries and atheromatous plaques following treatment with photosensitizing porphyrins", *Proc. SPIE-INT. Soc. Opt. Eng.,* 1462:77-80 (1990).

Database Crossfire Beilstein, Database Acession No. 4286587 (Reaction ID), for Levinson, E.G. et al., Russ. J. Bioorg. Chem (Engl. Transl.) 21(3):199-203 (1995) in Russian in the :Bioorg. Khim. 21(3):230-234 (1995).

Derwent English Abstract, Accession No. 1996-475153, citing Russian Patent RU 2054944 C, published Feb. 27, 1996, "Production of purpurin-18 for treatment of tumours—comprises extracting vegetable waste with ethanol, oxidative splitting, degreasing and purifying".

Dictionary of Cell Biology, Second Edition (Lackie & Dow, eds., 1989), p. 17.

Dillon et al., "In Vitro and In Vivo Protection Against Phototoxic Side Effects of Photodynamic Therapy by Radioprotective Agents WR-2721 and WR-77913", *Photochemistry and Photobiology, 48(2)*:235-238 (1988).

Dimitroff et al., "Anti-angiogenic activity of selected receptor tyrosine kinase inhibitors, PD166285 and PD173074: Implications for combination treatment with photodynamic therapy", *Investigational New Drugs, 17*:121-135 (1999).

Dougherty et al., Review "Photodynamic Therapy", *J. Natl. Cancer Inst., 90(12)*:889-905 (1998).

Dougherty et al., Yearly Review "Photodynamic Therapy", *Photochem. Photobiol., 58(6)*:895-900 (1993).

Dougherty, T.J., "A Brief History of Clinical Photodynamic Therapy Development at Roswell Park Cancer Institute", *J. Clin. Laser Med. & Surg., 14(5)*:219-221 (1996).

Dougherty, T.J., Photosensitization of malignant tumors, *Seminars in Surgical Oncology* 2:24-37 (1986).

Edamatsu et al., "One and Two-Photon Selective Excitation Spectroscopy of CuC1 Quantum Dots", *Review, 17*:15-16 (1998).

Fact Sheet: Laser Medical Pac, pp. 1-2 (1998).

Ferrario et al., "Antiangiogenic Treatment Enhances Photodynamic Therapy Responsiveness in a Mouse Mammary Carcinoma", *Cancer Research, 60*:4066-4069 (2000).

Fischer, H. et al., "[On the Bromination of the Esters of Mesoisochlorin $e_4$ and Mesochlorin $e_6$]," *Berischte der Deutschen Chemischen* 75:1778-1795 (1942).

Fisher, W.G. et al. "Simultaneous Two-Photon Activation of Type-1 Photodynamic Therapy Agents," *Photochem. Photobiol., 66(2)*:141-155 (1997).

Freiherr, G., "Advances in Photodynamic Therapy Lure Device Innovators", *Medical Device & Diagnostic Industry,* http://feedback@devicelink.com, 4 pages.

Gagel, M. P., Photodynamic therapy with porphyrins (1997), available at http://www.dermatology.org/laser/pdt.html.

Gilson et l., "Therapeutic ratio of photodynamic therapy in the treatment of superficial tumours of skin and subcutaneous tissues in man", *J. Cancer,* 58:665-667 (1988).

Granville et al., "Photodynamic Treatment with Benzoporphyrin Derivative Monoacid Ring A Produces Protein Tyrosine Phosphorylation Events and DNA Fragmentation in Murine P815 Cells", *Photochem. Photobiol., 67(3)*:358-362 (1998).

Gryshuk et al., "A First Comparative Study of Purpurinimide-based Fluorinated vs. Nonfluorinated Photosensitizers for Photodynamic Therapy", *Photochem. Photo biol.,* 76(5):555-559 (2002).

Haas et al., "Phototherapy of Bladder Cancer: Dose/Effect Relationships," *Journal of Urology,* 136:525-528 (1986).

Haslam et al., "Recent Developments in Methods for the Esterification and Protection of the Carboxyl Group," *Tetrahedron* 36:2409-2433 (1980).

Henderson et al., An in vivo quantitative structure-activity relationship for a congeneric series of pyropheophorbide derivatives as photosensitizers for photodynamic therapy, *Cancer Research* 57: 4000-4007 (1997).

Jacka et al., "A Lamp for Cancer Phototherapy", *Aust. J. Phys.*, 36:221-226 (1983).

Jiang et al., "Enhanced photodynamic killing of target cells by either monoclonal antibody or low density lipoprotein mediated delivery systems", *J. Controlled Release, 19*:41-58 (1992).

Jiang et al., "Selective Depletion of a Thymocyte Subset in Vitro with an Immunomodulatory Photosensitizer", *Clin. Immunol., 91(2)*:178-87 (1999).

Jones et al. "Photodynamic therapy for patients with advanced non-small-cell carcinoma of the lung," *Clin Lung Cancer*. 3(1):37-41 (2001).

Kashtan et al., "Photodynamic Therapy of Colorectal Cancer Using a New Light Source from In Vitro Studies to a Patient Treatment", *Dis. Colon. Rectum., 39(4)*:379-383 (1996).

Kessel et al., Photosensitization with bacteriochlorins, *Photochem. Photobiol.* 58(2): 200-203 (1993).

Kozyrev et al., Effect of substituents in $OsO_4$ reactions of metallochlorins regioselective synthesis of isobacteriochlorins and bacteriochlorins, *Tetrahedron Letters* 37(22): 3781-3784 (1996).

Kreimer-Birnbaum, M., "Modified Porphyrins, Chlorins, Phthalocyanines, and Purpurins: Second-Generation Photosensitizers for Photodynamic Therapy", *Seminars in Hematology 26(2)*: 157-173 (1989).

Latham et al., "Biophotonics Applications of High-Power Semiconductor Diode Laser technology", available at: http://www.arflhorizons.com/Briefs/0001/DE9903.html pp. 1-3 (1998) accessed on (Feb. 6, 2003).

Li et al., "Application of Ruppert's reagent in preparing novel perfluorinated porphyrins, chlorins and bacteriochlorins", *J. Chem. Soc. Perkin Trans* 1, 1785-1787 (1999).

Li et al., "Synthesis, comparative photosensitizing efficacy, human serum albumin (site II) binding ability, and intracellular localization characteristics of novel benzobacteriochlorins derived from vic-dihydroxybacteriochlorins,". *J Med Chem*. 46(25):5349-5359 (2003).

Lin et al., "Skin Necrosis due to Photodynamic Action of Benzoporphyrin Depends on Circulating Rather than Tissue Drug Levels: Implications for Control of Photodynamic Therapy", *Photochem. Photobiol., 68(4)*:575-583 (1998).

Lustig et al., "A multicenter Phase I safety study of intratumoral photoactivation of talaporfin sodium in patients with refractory solid tumors," *Cancer* 98(8):1767-71 (2003).

Marcus, S.L., "Photodynamic Therapy of Human Cancer", *Proceedings of the IEEE, 80(6)*;869-889 (1992).

Margaron et al., "Photodynamic therapy inhibits cell adhesion without altering integrin expression", *Biochimica et Biophysica Acta, 1359*:200-210 (1997).

McMillan et al., "Tumor growth inhibition and regression induced by photothermal vascular tergeting and angiogenesis inhibitor retinoic acid", *Cancer Lett., 137*:35-44 (1999).

Meerovich et al., "Photosensitizer for PDT based on phosphonate phthalocyanine derivative", *Proc. SPIE-INT. Scc. Opt. Eng., 2924*:86-90 (1996).

Merck Manual of Diagnosis and Therapy, 17th edition (Beers & Berkow, eds., 1999), pp. 816-817 and 1654-1657.

Mew et al., "Ability of Specific Monoclonal Antibodies and Conventional Antisera Conjugated to Hematoporphyrin to Label and Kill Selected Cell Lines Subsequent to Light Activation", *Cancer Res., 45*:4380-4386 (1985).

Mew et al., "Photoimmunotherapy: Treatment of Animal Tumors with Tumor-Specific Monoclonal Antibody-hematoporphyrin Conjugates", *Journal of Immunology, 130 (3)*:1473-1477 (1983).

Middleton et al., "Synthetic Biodegradable Polymers as Medical Devices", *Medical Plastics & Biomaterials*, pp. 30-39 (1998).

Millson et al., "Ex-vivo Treatment of Gastric Helicobacter Infection by Photodynamic Therapy", *J. of Photochemistry and Photobiology B: Biology, 32*:59-65 (1996).

Nakatani et al., "Chemistry and biochemistry of Chinese drugs. VII. Cytostatic pheophytins from silkworn excreta, and derived photocytotoxic pheophorbides", *Chem. Pharm. Bull., 29(8)*:2261-2269 (1981).

Nemoto et al., "Inhibition by a new biophosphonate (YM175) of bone resorption induced by the MBT-2 tumuor of mice", *Brit. J. Cancer, 67(5)*:893-897 (1993).

North et al., "Viral Inactivation in Blood and Red Cell Concentrates with Benzoporphyrin Derivative", *Blood Cells* 18:129-140 (1992).

Pandey et al., "Shedding some light on tumours", *Chem. Indust., 1998*:739-743 (1998).

Pandey et al., Comparative in vivo sensitizing efficacy of porphyrin and chlorin dimers joined with ester, ether, carbon-carbon or amide bonds, *J. Molecular Recognition* 9: 118-122 (1996).

Parrish, J.A., "Photobiologic Consideration Photoradiation Therapy", *Porphyrin Photosensitization*, pp. 91-108 (1983).

Patent Abstract of Japan citing Japanese Patent Application JP 09124652, published May 13, 1997, "Porphyrin Derivative and Use Thereof".

Pittau et al., "An Inexpensive Light Source for Oncologic Photodynamic Therapy", *IEEE Eng. Med. Biol.*, pp. 105-106 (1998).

Prewett et al., "Antivascular Endothelial Growth Factor Receptor (Fetal Liver Kinase 1) Monoclonal Antibody Inhibits Tumor Angiogenesis and Growth of Several Mouse and Human Tumors", *Cancer Research, 59*:5209-5218 (1999).

Renno et al., "Photodynamic Therapy Using Lu-Tex Induces Apoptosis In Vitro, and Its Effect is Potentiated by Angiostatin in Retinal Capillary Endothelial Cells", *Investigative Opthalmol. & Visual Sci., 41(12)*:3963-3971 (2000).

Rimington et al., Preparation and photosensitizing properties of hematoporphyrin ethers, *Free Rad. Res. Comms.* 7(3-6): 139-142 (1989).

Roy et al., "Ceramic-based nanoparticles entrapping water-soluble photosensitizing anticancer drugs: a novel drug-carrier system for photodynamic therapy," *J Am Chem Soc*. 125(26):7860-5 (2003).

Ruebner, A. et al. "Carrier Systems in PDT II: Accumulation Strategies of Biotin-Avidin Coupled Photosensitizers Developed On Cultured Tumor Cells," *SPIE, 2625*:328-32 (1996).

Rungta et al., Purpurinimides as photosensitizers: effect of the presence and position of the substituents in the in vivo photodynamic efficacy, *Bioorg. Medicinal Chem. Letters* 10: 1463-1466 (2000).

Savellano et al., "Pegylated BPD Verteporfin C225 Anti-EGF Receptor Direct Covalent Linkage Photosensitizer Immunoconjugates", *Photochem. Photobiol., 69*:38S (1999).

Savitsky, A.P. et al. "Avidin-Biotin System for Targeting

Delivery of Photosensitizers and Other Cytotoxic Agents Into Malignant Tissues," *SPIE, 3191*: 243-53 (1997).

Schmidt et al., "Size-dependent Two-Photon Excitation pectroscopy of CdSe Nanocrystals", *Physical Review B, 53(19)*:12629-12632 (1996).

Schmidt-Erfurth et al., "In Vivo Uptake of Liposomal Benzoporphyrin Derivative and Photothrombosis in Experimental Corneal Neovascularization", *Lasers in Surgery and Medicine, 17*:178-188 (1995).

Schmidt-Erfurth et al., "Photodynamic Therapy of Experimental Choroidal Melanoma Using Lipoprotein-delivered Benzoporphyrin", *Opthalmol., 101*:89-99 (1994).

Schmidt-Erfurth et al., "Photodynamic therapy of subfoveal choroidal neovascularization: clinical and angiographic examples", *Graefe's Arch. Clin. Exp. Opthalmol., 236*:365-74 (1998).

Schmidt-Erfurth et al., "Vascular targeting in photodynamic occlusion of subretinal vessels", *Opthalmol., 101(12)*:1953-1961 (1994).

Sharman et al., "Novel water-soluble phthalocyanines substituted with phosphonate moieties on the benzo rings", *Tetrahedron Lett., 37(33)*:5831-5834 (1996).

Sigsestad, C.P. et al. "Chemical Modification of Normal Tissue Damage Induced by Photodynamic Therapy," *Brit. J. Cancer 74(Suppl.37)*;S89-92 (1996).

Smith et al, "Meso substitution of chlorophyll derivatives: direct route for transformation of bacteriopheophorbides d into bacteriopheophorbides c," *J Am Chem Soc* 107:4946-54 (1985).

Smith et al., "Bacteriochlorophylls c from *Chloropseudomonas ethylicum*. Composition and NMR Studies of the Pheophorbides and Derivatives", Am. Chem. Soc., 102(7):2437-2448 (1980).

Spikes, J.D., Porphyrins and related compounds as photodynamic sensitizers, *Annals of the New York Academy of Sciences* 244: 496-508 (1975).

Stedman's Medical Dictionary, 26th Edition, (Williams & Wilkens, 1995), pp. 268, 276-280, 726-727, 1165, 1182, and 1571-1572.

Stemberg et al., "Porphyrin-based Photosensitizers for Use in Photodynamic Therapy", *Tetrahedron*, 54:4151-4202 (1998).

Su, F., Photodynamic Therapy: A Maturing Medical Technology, OE-Reports, SPIE, Feb. 2000, available at http://www.spie.org/web/oer/february/feb00/phototherapy.html.

Szeimies et al., "A New Light Source for PDT of Skin Lesions", http://www.lumacare.com/paper3.htm, 2 pages (after 1993).

Szeimies et al., "A Possible New Incoherent Lamp for Photodynamic Treatment of Superficial Skin Lesions", *Acta Derm Venereol, 74*:117-119 (1994).

Taber's Cyclopedic Medical Dictionary, 14th edition (C. L. Thomas, ed., 1983), p. 63.

Tomio et al., "Effect of Hematoporphyrin and Red Light on AH-130 Solid Tumors in Rats", *ACTA Radiologica Oncol., 22*:49-53 (1983).

Umemura et al., "Recent Advances in Sonodynamic Approach to Cancer Therapy," *Ultrasonics Sonochemistry*, 3:S187-S191 (1996).

Warwick, R.I., "Infinite Machines' Subsidiary Receives Positive Results in Photodynamic Therapy Tests", *BW HealthWire*, http://biz.yahoo.com/bw/97/06/18/imci_y000_1.html, 2 pages (1997).

Whitehurst et al., "Development of an Alternative Light Source to Lasers for Photodynamic Therapy: 1. Comparative In Vitro dose Response Characteristics", *Lasers in Med. Sci.*, 8:259-267 (1993).

Wieman et al., "(418) Photodynamic Therapy (PDT) of Locally Recurrent Breast Cancer (LRBC) with Lutetium Texaphyrin (Lutrin)", *American Society of Clinical Oncology, 18*:111A (1999).

Wilder-Smith et al., "(G1546) Photoeradication of *Helicobacter pylori* in Humans: Phase 1 Study", *AGA Abstracts Gastroenterology, 116(4)*:A354 (1999).

Wood et al., "A beam-splitting device for use with fiber-coupled laser light sources for photodynamic therapy," *Photochem Photobiol.* 76(6):683-5 (2002).

Woodburn et al., Evaluation of porphyrin characteristics required for photodynamic therapy, *Photochem. Photobiol.* 55(5): 697-704 (1992).

Yamamoto et al., "Photodynamic effects on the nucleic acids of cancer cells sensitized by sodium phytochlorin", *Medicine and Biology, 90(6)*:397-400, English translation and certificate of translation included, 4 pages (Jun. 10, 1975).

Yamamoto et al., "Photoradiation therapy, phytochlorin and visible light", *Prevention and Detection of Cancer*, Part 1, *Prevention*. Volume 2, *Etiology-Prevention Methods*, Proceedings of the Third International Symposium on Detection and Prevention of Cancer held Apr. 26, 1976 in New York, N.Y., 1(2):1789-1802 (1978).

Yamamoto, T., "Effect of phytochlorin on transplantable cancer cells", *Medicine and Biology, 89(6)*:433-438, English translation and certificate of translation included, 7 pages (Dec. 10, 1974).

Yamamoto, T., "Suppression of tumors by the photodynamic action of phytochlorin sodium", *Medicine and Biology, 90(4)*:161-164, English translation and certificate of translation included, 4 pages (Apr. 10, 1975).

Yumita et al., "Sonodynamically Induced Antitumor Effect of Gallium-Porphyrin Complex by focused Ultrasound on Experimental Kidney Tumor", *Cancer Letters, 112*:79-86 (1997).

Yumita et al., "The Combination Treatment of Ultrasound and Antitumor Drugs on Yoshida Sarcoma", *Japan J. Hyperthermic Oncol., 3(2)*:175-182 (1987).

Zheng et al., "Photosensitizers Related to Purpurin-18-N-alkylimides: A Comparative in vivo Tumoricidal Ability of Ester versus Amide Functionalities", *Bioorganic & Med. Chem. Letts.*, 10:123-127 (2000).

Zheng et al., "Chlorin-based symmetrical and unsymmetrical dimers with amide linkages: effect of the substituents on photodynamic and photophysical properties," *J. Chem. Soc. Perkins 1*, pp. 3113-3121 (2000).

Zheng et al., "PDT using a novel LED light source and LS11 in a rat liver model," *30th Annual Meeting of the American Society for Photobiology*; Jul. 13-17, 2002; Quebec City, Canada. American Society for Photobiology: 33 [abstract 95].

* cited by examiner

PHOTODYNAMIC TREATMENT OF TARGETED CELLS

RELATED APPLICATIONS

This application is a continuation of and claims priority to allowed U.S. application Ser. No. 09/905,501, filed Jul. 13, 2001 and now U.S. Pat. No. 6,899,723 to James Chen, entitled "TRANSCUTANEOUS PHOTODYNAMIC THERAPY OF TARGETED CELLS," filed Jul. 13, 2001, the disclosure of which is incorporated by reference in its entirety herein.

TECHNICAL FIELD

This invention generally relates to the field of delivery to a tumor site of a therapeutically effective amount of a photosensitizing agent that is activated by a relatively low fluence rate of light administered over a prolonged period of time. More specifically, the filed of this invention relates to the delivery of a photosensitizing agent that is targeted to link or to preferentially associate with target cells at the target site, including cancer cells.

BACKGROUND ART

One form of energy activated therapy for destroying abnormal or diseased tissue is photodynamic therapy (PDT). PDT is a two-step treatment process, which has received increasing interest as a mode of treatment for a wide variety of different cancers and diseased tissue. The first step in this therapy is carried out by administering a photosensitive compound systemically by ingestion or injection, or topically applying the compound to a specific treatment site on a patient's body, followed by illumination of the treatment site with light having a wavelength or waveband corresponding to a characteristic absorption waveband of the photosensitizer. The light activates the photosensitizing compound, causing singlet oxygen radicals and other reactive species to be generated, leading to a number of biological effects that destroy the abnormal or diseased tissue, which has absorbed the photosensitizing compound. The depth and volume of the cytotoxic effect on the abnormal tissue, such as a cancerous tumor, depends in part on the depth of the light penetration into the tissue, the photosensitizer concentration and its cellular distribution, and the availability of molecular oxygen, which will depend upon the vasculature system supplying the abnormal tissue or tumor.

Various types of PDT light sources and their methods of use have been described in the prior art literature. However, publications describing appropriate light sources and the effects of transcutaneous light delivery to internal treatment sites within a patient's body, for PDT purposes, are relatively limited in number. It has generally been accepted that the ability of a light source external to the body to cause clinically useful cytotoxicity during PDT is limited in depth to a range of 1–2 cm or less, depending on the photosensitizer.

Treatment of superficial tumors in this manner has been associated with inadvertent skin damage due to accumulation of the photosensitizer in normal skin tissue, which is a property of all systemically administered photosensitizers in clinical use. For example, clinically useful porphyrins such as PHOTOPHRIN™ (a QLT, Ltd. brand of sodium porfimer) are associated with general dermal photosensitivity lasting up to six weeks. PURLYTIN™, which is a brand of purpurin, and FOSCAN™, which is brand of chlorin, sensitize the skin to light for at least several weeks, so that patients to whom these drugs are administered must avoid exposure to sunlight or other bright light sources during this time to avoid unintended phototoxic effects on the normal dermal tissue. Indeed, efforts have been made to develop photoprotectants to reduce skin photosensitivity (see, for example: Dillon et al., "Photochemistry and Photobiology," 48(2): 235–238 (1988); and Sigdestad et al., British J. of Cancer, 74: S89–S92, (1996)).

Recently, it has been reported that a relatively intense external laser light source might be employed transcutaneously to cause two-photon absorption by a photosensitizer at a greater depth within a patient's body, so that it is theoretically possible to cause a very limited volume of cytotoxicity in diseased tissue at greater depths than previously believed possible. However, no clinical studies exist to support this contention. One would expect that the passage of an intense beam of light through the skin would lead to the same risk of phototoxic injury to non-target normal tissues, such as skin and subcutaneous normal tissue, if this light is applied in conjunction with a systemically administered photosensitizer.

For example, one PDT modality discloses the use of an intense laser source to activate a photosensitizer drug within a precisely defined boundary (see: U.S. Pat. No. 5,829,448, Fisher et al., "Method for improved selectivity in photoactivation of molecular agents"). The two-photon methodology requires a high power, high intensity laser for drug activation using a highly collimated beam, with a high degree of spatial control. For a large tumor, this treatment is not practical, since the beam would have to be swept across the skin surface in some sort of set, repeating pattern, so that the beam encompasses the entire volume of the tumor. Patient or organ movement would be a problem, because the beam could become misaligned. Exposure of normal tissue or skin in the path of the beam and subcutaneous tissue photosensitivity is not addressed in the prior art literature. Any photosensitizer absorbed by normal tissue in the path of the beam will likely be activated and cause unwanted collateral normal tissue damage. Clearly, it would be preferable to employ a technique that minimizes the risk of damage to normal tissue and which does not depend upon a high intensity laser light source to produce two photon effects. Further, it would be preferable to provide a prolonged exposure of an internal treatment site with light at a lower fluence rate, which tends to reduce the risk of harm to non-target tissue or skin and subcutaneous normal tissue and reduces any collateral tissue damage due to phototoxicity.

Other PDT modalities have employed the use of a light source producing a low total fluence delivered over a short time period to avoid harm to skin caused by activation of a photosensitizer and have timed the administration of such drugs to better facilitate destruction of small tumors in animals (see, for example, U.S. Pat. No. 5,705,518, Richter et al.). However, although not taught nor suggested by the prior art, it would be preferable to employ a light source that enables a relatively large total fluence PDT, but at a lower intensity so that larger tumor volumes can more readily be treated as well as diffused diseases, including metastasized tumors and other pathological tissue formation resulting from infectious or pathogenic agents, such as bacterial infections or other disease states, such as immunological diseases.

If, as is often the case, a target tumor tissue lies below an intact cutaneous layer of normal tissue, the main drawbacks of all transcutaneous illumination methods, whether they be external laser or external non-laser light sources, are: (1) the risk of damage to non-target tissues, such as the more superficial cutaneous and subcutaneous tissues overlying the target tumor mass; (2) the limited volume of a tumor that can be treated; and (3) the limitation of treatment depth. Damage to normal tissue lying between the light source and the target tissue in a tumor occurs due to the uptake of photosensitizer by the skin and other tissues overlying the tumor mass, and the resulting undesired photoactivation of the photosensitizer absorbed by these tissues. The consequences of inadvertent skin damage caused by transcutaneous light delivery to a subcutaneous tumor may include severe pain, serious infection, and fistula formation. The limited volume of tumor that can be clinically treated and the limitations of the light penetration below the skin surface in turn have led those skilled in this art to conclude that clinical transcutaneous PDT is only suitable for treatment of superficial, thin lesions.

U.S. Pat. No. 5,445,608, Chen et al, discloses the use of implanted light sources for internally administering PDT. Typically, the treatment of any internal cancerous lesions with PDT requires at least a minimally invasive procedure such as an endoscopic technique, for positioning the light source proximate to the tumor, or open surgery to expose the tumor site. There is some risk associated with any internal procedure performed on the body. Clearly, there would be significant advantage to a completely noninvasive form of PDT directed to subcutaneous and deep tumors, which avoids the inadvertent activation of any photosensitizer in skin and intervening tissues. To date, this capability has not been clinically demonstrated nor realized. Only in animal studies utilizing mice or other rodents with very thin cutaneous tissue layers, have very small superficial subcutaneous tumors been treated with transcutaneously transmitted light. These minimal in vivo studies do not provide an enabling disclosure or even suggest how transcutaneous light sources might safely be used to treat large tumors in humans with PDT, however.

Another PDT modality in the prior art teaches the destruction of abnormal cells that are circulating in the blood using light therapy, while leaving the blood vessels intact (see, for example: U.S. Pat. No. 5,736,563, Richter et al.; WO 94/06424, Richter; WO 93/00005, Chapman et al.; U.S. Pat. No. 5,484,803, Richter et al., and WO 93/24127, North et al.). Instead, it might be preferable to deliberately damage and occlude blood vessels that form the vasculature supplying nutrients and oxygen to a tumor mass, thus rendering a given volume of abnormal tissue in the tumor (not circulating cells) ischemic and anoxic and thus promoting the death of the tumor tissue serviced by these blood vessels.

To facilitate the selective destruction of the blood vessels that service a tumor, it would be desirable to selectively bind a photosensitizing agent to specific target tissue antigens, such as those found on the epithelial cells comprising tumor blood vessels. This targeting scheme should decrease the amount of photosensitizing drug required for effective PDT, which in turn should reduce the total light energy, and the light intensity needed for effective photoactivation of the drug. Even if only a portion of a blood vessel is occluded as a result of the PDT, downstream thrombosis is likely to occur, leading to a much greater volume of tumor necrosis compared to a direct cytotoxic method of destroying the tumor cells, in which the photosensitizer drug must be delivered to all abnormal cells that are to be destroyed. One method of ensuring highly specific uptake of a photosensitizer by epithelial cells in tumor vessels would be to use the avidin-biotin targeting system. Highly specific binding of a targeted agent such as a PDT drug to tumor blood vessels (but not to the cells in normal blood vessels) is enabled by this two step system. While there are reports in the scientific literature describing the binding between biotin and streptavidin to target tumor cells, there are no reports of using this ligand-receptor binding pair to bind with cells in tumor vessels nor in conjunction with carrying out prolonged PDT light exposure (see, for example: Savitsky et al., SPIE, 3191:343–353, (1997); and Ruebner et al., SPIE, 2625: 328–332, (1996)). In a non-PDT modality, the biotin-streptavidin ligand-receptor binding pair has also been reported as useful in binding tumor targeting conjugates with radionuclides (see U.S. Pat. No. 5,630,996, Reno et al.) and with monoclonal antibodies (see Casalini et al., *J. Nuclear Med.*, 38(9):1378–1381, (1997) and U.S. Pat. No. 5,482,698, Griffiths).

Other ligand-receptor binding pairs have been used in PDT for targeting tumor antigens, but the prior art fails to teach their use in conjunction with targeting cells in blood vessels or treatment of large, established tumors (see, for example, Mew et al., *J. of Immunol.*, 130(3): 1473–1477, (1983)).

High-powered lasers are usually employed as a light source in administering PDT to shorten the time required for the treatment (see W. G. Fisher, et al., *Photochemistry and Photobiology*, 66(2): 141–155, (1997)). However, it would likely be safer to use a low power, non-coherent light source that remains energized for two or more hours to increase the depth of the photoactivation. However, this approach is contrary to the prior art that recommends PDT be carried out with a brief exposure from a high powered, collimated light source.

Recently, there has been much interest in the use of anti-angiogenesis drugs for treating cancerous tumors by minimizing the blood supply that feeds a tumor's growth. However, targeting of tumor vessels using anti-angiogenesis drugs may lead to reduction in size of small tumors and may prevent new tumor growth, but will likely be ineffective in causing reliable regression of large, established tumors in humans. However, by using a combination of anti-angiogenesis and a photosensitizer in the targeting conjugate, it is likely that a large volume tumor can be destroyed by administering PDT.

In treating large tumors, a staged procedure may be preferable in order to control tumor swelling and the amount of necrotic tissue produced as the PDT causes destruction of the tumor mass. For example, by activating a photosensitizer bound to tumor vessels in the center of a large tumor and then sequentially expanding the treatment zone outward in a stepwise manner, a large volume tumor can be gradually ablated in a controlled fashion in order to prevent swelling due to edema and inflammation, which is problematic in organs such as the brain.

Delivered in vivo, PDT has been demonstrated to cause vessel thrombosis and vascular constriction, occlusion, and collapse. And though the treatment of very superficial, thin tumors has been reported using transcutaneous light, there are no clinical reports of transcutaneous light activation being used to destroy deeper, thick tumors that are disposed more than 2 cm below the skin surface. Clearly, there is a need for a PDT paradigm that enables large volume tumors that are disposed well below the surface of the skin to be destroyed with transcutaneous light activation.

PDT of locally recurrent breast cancer (LRBC) with lutetium texaphyrin has been reported by T. J. Wieman et al., in program/proceedings, *American Society of Clinical Oncology*, Vol. 18, P. 111A (1999). This study by Wieman et al. involved the treatment of superficial recurrent chest wall breast cancer. Lutrin™ (lutetium texaphyrin, brand; Pharmacyclics, Inc, Sunnyvale, Calif.) was administered by injection at a dose of 1.5 mg/Kg to 4.0 mg/Kg and followed by chest wall illumination by 150 joules or 100 joules of light at 732 nm using laser or LED device. However, this study did not suggest or disclose the use of transcutaneous light delivery to treat a subcutaneous tumor mass. Further, at the light dosage employed, a sustained delivery of light at the reported intensity may not be possible without adverse reactions.

It is apparent that the usual method of administering PDT to treat bulky tumors, which relies on invasive introduction of optical fibers, is not the best approach. It would be highly advantageous to apply light transcutaneously in a completely noninvasive method to treat such large tumors (as well as small and even microscopic tumors), without risking damage to non-target tissues, such as skin and normal subcutaneous tissue. Instead of the conventional technique, a method of photoactivation and a series of photosensitizer constructs is needed that enable PDT induced cytotoxicity, on both a macro and microscopic scale, without risk to the cutaneous layer, or any surrounding normal tissues. Also, the therapeutic index should be enhanced if a specific photosensitizer drug targeting scheme is employed.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this specification are hereby incorporated by reference herein, in their entirety.

DISCLOSURE OF THE INVENTION

In accord with the present invention, a method is defined for transcutaneously administering a photodynamic therapy to a target tissue in a mammalian subject. The method includes the step of administering to the subject a therapeutically effective amount of either a photosensitizing agent having a characteristic light absorption waveband, a photosensitizing agent delivery system that delivers the photosensitizing agent, or a prodrug that produces a prodrug product having a characteristic light absorption waveband. The photosensitizing agent, photosensitizing agent delivery system, or prodrug selectively binds to the target tissue. Light having a waveband corresponding at least in part with the characteristic light absorption waveband of said photosensitizing agent or of the prodrug is used for transcutaneously irradiating at least a portion of the mammalian subject. An intensity of the light used for irradiating is substantially less than 500 mW/cm$^2$, and a total fluence of the light is sufficiently high to activate the photosensitizing agent or the prodrug product, as applicable.

Preferably, sufficient time is allowed for any of the photosensitizing agent, the photosensitizing agent delivery system, or the prodrug (depending upon which one of these was administered) that is not bound or preferentially associated to the target tissue to clear from non-target tissues of the mammalian subject prior to the step of irradiating with the light.

By initiating light activation soon after targeted PDT drug administration, blood vessel closure/thrombosis is initiated within the lumen by injury to circulating blood elements and not solely by direct damage to targeted endothelium. For example, platelet activation and red blood cell injury occurs as a result of light activation at a time when the free circulating targeted drug concentration is high. This process leads to thrombosis formation and occlusion of the blood vessel, by way of damage to circulating blood elements and not by way of direct endothelial damage. The duration of light activation preferably should be long enough to prevent blood vessel recanalization. This recanalization would most likely lead to tumor survival, thus the preferred illumination duration should result in permanent tumor infarction.

Preferably, when targeting tumors with PDT drugs, actively growing "budding" cells are targeted as well. Activation in this area is timed and occurs as the plasma concentration of drug is falling in normal tissue, thus protecting normal tissue from intravascular non-specific activation. Since time is required for binding to abnormal vessels, and normal tissue clearance to occur, this activation is delayed until selective binding has occurred at the tumor margins.

In one application of the invention, the target tissue is vascular endothelial tissue. In another application, the target tissue is an abnormal vascular wall of a tumor. As further defined, the target tissue is selected from the group consisting of: vascular endothelial tissue, an abnormal vascular wall of a tumor, a solid tumor, a tumor of a head, a tumor of a neck, a tumor of a gastrointestinal tract, a tumor of a liver, a tumor of a breast, a tumor of a prostate, a tumor of a lung, a nonsolid tumor, malignant cells of one of a hematopoietic tissue and a lymphoid tissue, lesions in a vascular system, a diseased bone marrow, and diseased cells in which the disease is one of an autoimmune and an inflammatory disease. In yet a further application of the present invention, the target tissue is a lesion in a vascular system. It is contemplated that the target tissue is a lesion of a type selected from the group consisting of atherosclerotic lesions, arteriovenous malformations, aneurysms, and venous lesions.

The step of irradiating generally comprises the step of providing a light source that is activated to produce the light. In one preferred embodiment of the invention, the light source is disposed external to an intact skin layer of the mammalian subject during the step of irradiating by transcutaneous irradiation. In another preferred embodiment, the method includes the step of inserting the light source underneath an intact skin layer, but external to an intact surface of an organ of the mammalian subject, where the organ comprises the target tissue, as provided in organ transillumination irradiation.

A still further preferred embodiment of the present invention provides the use of a light source that may include one or more sources of illumination, such as an LED array. This method also includes the step of inserting the light source underneath an intact skin layer and underneath the parenchymal or capsular membrane layer of an organ, where the organ comprises the target tissue, as provided in interstitial transillumination irradiation.

Preferably, the photosensitizing agent is conjugated to a ligand. The ligand may be either an antibody or an antibody fragment that is specific in binding with the target tissue. Alternatively, the ligand is a peptide, or a polymer, either of which is specific in binding with the target tissue.

Preferably, photosensitizing agents or prodrugs are of a chemical composition that allows them to cross fenestrations and gaps in tumor vessels and bind to the ablumenal as well as the lumenal side of the blood vessels. As target cell (e.g., a selected tumor cell type) cytotoxicity occurs adjacent to blood vessels, cell swelling and release of cellular contents leads to further inflammation which augments the occlusion process from the ablumenal side.

The photosensitizing agent is preferably selected from the group consisting of indocyanine green (ICG), methylene blue, toluidine blue, aminolevulinic acid (ALA), chlorins, bacteriochlorophylls, phthalocyanines, porphyrins, purpurins, texaphyrins, and other photoreactive agents that have a characteristic light absorption peak in a range of from about 500 nm to about 1100 nm. Additionally, the photosensitizing agent should clear quickly from normal tissue, but not from target tissues.

One photosensitizing agent, Lutrin™ (lutetium texaphyrin, brand; Pharmacyclics, Inc., Sunnyvale, Calif.) exhibits clearance from normal tissues in about 24 hours while tumor tissues retain this agent from 24–96 hours from time of administration. Lutetium texaphyrin absorbs light at bout 732 nm and is administered by injection, exhibiting sufficient selectivity in uptake as to enable transcutaneous PDT of tumors that are deep in an intact layer of tissue.

Another application of the present invention uses an energy-activated compound that has a characteristic energy absorption waveband. The energy-activated compound selectively binds to the target tissue. Energy having a waveband corresponding at least in part with the characteristic energy absorption waveband of said energy activated compound is used for transcutaneously irradiating at least a portion of the mammalian subject. Preferably the waveband is in the ultrasonic range of energy. Said compound is activated by said irradiating step, wherein the intensity of said ultrasonic energy is substantially less than that level which would result in damage to normal tissue, but at a sufficiently high total fluence of ultrasonic energy that is absorbed by said compound which in turn destroys the target tissue to which it is bound. Preferably, the total fluence of the ultrasonic energy used for irradiating is between about 5 Khz and more than about 300 Mhz, more preferably, between about 10 kHz and more than about 200 Mhz, and most preferably, between about 20 kHz and more than about 100 MHz.

The step of irradiating is preferably carried out for a time interval of from about 4 minutes to about 72 hours, or more preferably, from about 60 minutes to about 48 hours, or most preferably, from about 3 hours to about 24 hours, depending upon the photosensitizing or photosensitizer agent used.

In yet another application of the invention, the target tissue is bone marrow, or comprises cells afflicted with either an autoimmune disease or an inflammatory disease. A still further application of the present invention, relates to methods for the treatment of diffused disease, where the target tissue may include metastasized tumor cells; immunological cells; tissues infected with pathogenic agents or any other diseased or damaged tissues that are interspersed with normal or healthy tissue.

The present invention also includes methods for administering photo-dynamic therapy to a target tissue in a mammalian subject, where the target tissue is irreversibly damaged or destroyed resulting in extensive necrosis.

Preferably, the total fluence of the light used for irradiating is between about 30 Joules and about 25,000 Joules, more preferably, between about 100 Joules and about 20,000 Joules, and most preferably, between about 500 Joules and about 10,000 Joules.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

INTRODUCTION AND GENERAL DESCRIPTION OF THE INVENTION

Figure 1:
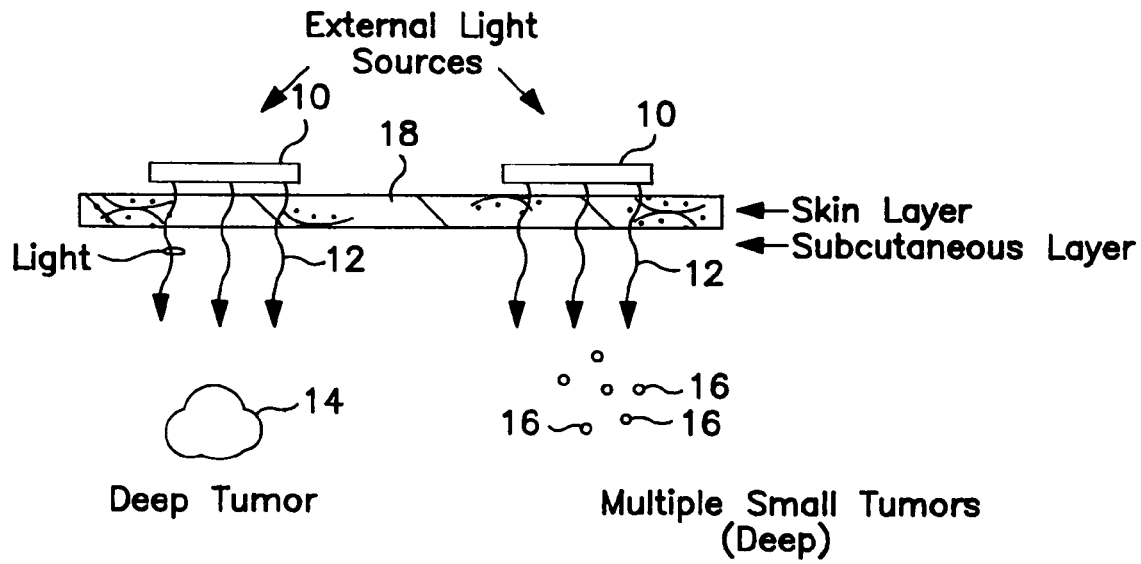
FIG. 1 is a schematic diagram illustrating an external light source being used to administer transcutaneous cancer therapy to a relatively large, singular tumor, and to multiple, small tumors.

This invention is directed to methods and compositions for therapeutically treating a target tissue or destroying or impairing a target cell or a biological component in a mammalian subject by the specific and selective binding of a photosensitizer agent to the target tissue, cell, or biological component. At least a portion of the subject is irradiated with light at a wavelength or waveband within a characteristic absorption waveband of the photosensitizing agent. The light is administered at a relatively low fluence rate, but at an overall high total fluence dose, resulting in minimal collateral normal tissue damage. It is contemplated that an optimal total fluence for the light administered to a patient will be determined clinically, using a light dose escalation trial. It is further contemplated that the total fluence administered during a treatment will preferably be in the range of 30 Joules to 25,000 Joules, more preferably, in the range from 100 Joules to 20,000 Joules, and most preferably, in the range from 500 Joules to 10,000 Joules.

The terminology used herein is generally intended to have the art recognized meaning and any differences therefrom as used in the present disclosure, will be apparent to the ordinary skilled artisan. For the sake of clarity, terms may also have a particular meaning, as well be clear from their use in context. For example, "transcutaneous" as used in regard to light irradiation in this specification and in the claims that follow, more specifically herein refers to the passage of light through unbroken tissue. Where the tissue layer is skin or dermis, transcutaneous includes "transdermal" and it will be understood that the light source is external to the outer skin layer. However, the term "transillumination" as used herein refers to the passage of light through a tissue layer. For example, "organ transillumination" refers to light irradiation through the outer surface layer of an organ, e.g., the liver, and it will be apparent that the light source is external to the organ, but internal or implanted within the subject or patient. Similarly and more generally, "interstitial transillumination" refers to light irradiation from a light source that is implanted or surgically positioned underneath the epidermal layer of tissue within an organ, such as the parenchymal or capsular layer of tissue of the organ or tumor mass, where the organ or tumor mass comprises the target tissue.

One aspect of the present invention provides for the precise targeting of photosensitive agents or drugs and compounds to specific target antigens of a subject or patient and to the method for activating the targeted photosensitizer agents by subsequently administering to the subject light at a relatively low fluence rate, over a prolonged period of time, from a light source that is external to the target tissue in order to achieve maximal cytotoxicity of the abnormal tissue, with minimal adverse side effects or collateral normal tissue damage.

A photosensitizing agent or drug targeted to a specific receptor will, preferably, attach to all such receptors. Receptors such as the endothelial VEGF receptor are expressed not only by endothelial cells, but also by tumor cells themselves. Thus, when the agent is targeted to this type of receptor there will be more targets than solely endothelial cells and correspondingly more biological effect after irradiation.

FIG. 1 illustrates transcutaneous delivery of light 12 from an external source 10 to a relatively deep tumor 14, or to a plurality of small, but relatively deep tumors 16. The light emitted by external source 10 is preferably of a longer waveband, but still within an absorption waveband of the photosensitive agent (not shown in this Figure) that has been selectively linked to tumor 14 and smaller tumors 16. The longer wavelength of light 12 enables it to pass through a dermal layer 18 and penetrate into the patient's body beyond the depth of tumor(s) being treated with targeted PDT. In these two examples, the PDT is directed specifically at target cells in tumor 14 or in tumors 16.

As used in this specification and the following claims, the terms "target cells" or "target tissues" refer to those cells or tissues, respectively that are intended to be impaired or destroyed by PDT delivered in accord with the present invention. Target cells or target tissues take up or link with the photosensitizing agent, and, when sufficient light radiation of the waveband corresponding to the characteristic waveband of the photo-sensitizing agent is applied, these cells or tissues are impaired or destroyed. Target cells are cells in target tissue, and the target tissue includes, but is not limited to, vascular endothelial tissue, abnormal vascular walls of tumors, solid tumors such as (but not limited to) tumors of the head and neck, tumors of the gastrointestinal tract, tumors of the liver, tumors of the breast, tumors of the prostate, tumors of the lung, nonsolid tumors and malignant cells of the hematopoietic and lymphoid tissue, other lesions in the vascular system, bone marrow, and tissue or cells related to autoimmune disease.

Further, target cells include virus-containing cells, and parasite-containing cells. Also included among target cells are cells undergoing substantially more rapid division as compared to non-target cells. The term "target cells" also includes, but is not limited to, microorganisms such as bacteria, viruses, fungi, parasites, and infectious agents. Thus, the term "target cell" is not limited to living cells but also includes infectious organic particles such as viruses. "Target compositions" or "target biological components" include, but are not be limited to: toxins, peptides, polymers, and other compounds that may be selectively and specifically identified as an organic target that is intended to be impaired, irreversibly damaged or destroyed by this treatment method.

Figure 2:
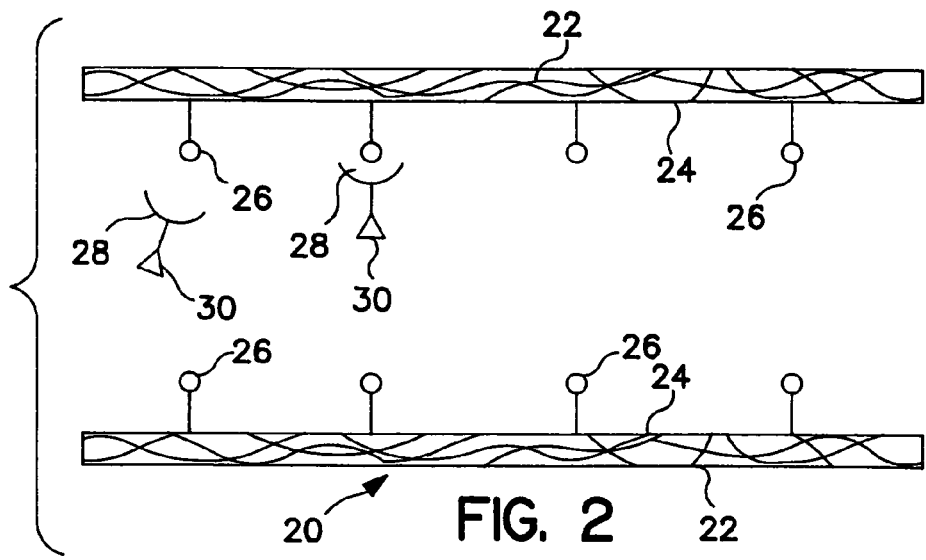
FIG. 2 is a schematic cross-sectional view of a section of a tumor blood vessel, illustrating linking of an antibody/photosensitive drug to endothelial tissue.

FIG. 2 includes a section of a tumor blood vessel 20 having a wall 22, with an endothelial lining 24. A plurality of endothelial antigens 26 are disposed along the endothelial lining. In this example, antibodies 28 that are specific to endothelial antigens 26 have been administered and are shown linking with the endothelial antigens. Coupled to antibodies 28 are PDT photosensitive drug molecules 30. Thus, the PDT photosensitive drug molecules are linked to the endothelial antigens via antibodies 28, but are not linked to non-target cells, since the antibodies are selective only to the endothelial antigens.

"Non-target cells" are all the cells of a mammal that are not intended to be impaired, damaged, or destroyed by the treatment method rendered in accord with the present invention. These non-target cells include but are not limited to healthy blood cells, and other normal tissue, nor otherwise identified to be targeted. In yet another application of the invention, the target tissue is bone marrow, or comprises cells afflicted with either an autoimmune disease or an inflammatory disease. A still further application of the present invention, relates to methods for the treatment of diffused disease, where the target tissue may include metastasized tumor cells; immunological cells; tissues infected with pathogenic agents or any other diseased or damaged tissues that are interspersed with normal or healthy tissue. "Diffused disease" is used herein to refer to a pathologic condition, wherein impaired or damaged tissue is not localized but found in multiple sites throughout the mammalian subject.

"Destroy" means to kill or irreversibly damage the desired target cell. "Impair" means to change the target cell in such a way as to interfere with its function. For example, in North et al., it is observed that after virus-infected T cells treated with benzoporphyrin derivatives ("BPD") were exposed to light, holes developed in the T cell membrane and increased in size until the membrane completely decomposed (*Blood Cells* 18: 129–40, (1992)). Target cells are understood to be impaired or destroyed even if the target cells are ultimately disposed of by macrophages.

The present invention also includes methods for administering photodynamic therapy to a target tissue in a mammalian subject, where the target tissue is irreversibly damaged or destroyed resulting in extensive necrosis. "Extensive necrosis" is used herein to refer to the formation of a zone of necrotic tissue greater than about 3 cm circumference around a light source implanted probe or greater than about 1 cm radius from the position of the light source. More preferably, the zone of necrosis is greater than about 5 cm around a light source implanted probe or greater than about 2 cm radius from the position of the light source.

"Energy activated agent" is a chemical compound that binds to one or more types of selected target cells and, when exposed to energy of an appropriate waveband, absorbs the energy, causing substances to be produced that impair or destroy the target cells.

"Photosensitizing or photosensitizer agent" is a chemical compound that is absorbed by or preferentially associates with one or more types of selected target cells and when exposed to light of an appropriate waveband, absorbs the light, causing substances to be produced that impair or destroy the target cells. Virtually any chemical compound that preferentially is absorbed or linked to a selected target and absorbs light causing the desired therapy to be effected may be used in this invention. Preferably, the photosensitizing agent or compound is nontoxic to the animal to which it is administered or is capable of being formulated in a nontoxic composition that can be administered to the animal. In addition, following exposure to light, the photosensitizing agent in any resulting photodegraded form is also preferably nontoxic. A comprehensive listing of photosensitive chemicals may be found in Kreimer-Birnbaum, *Sem. Hematol* 26: 157–73, (189). Photosensitive agents or compounds include, but are not limited to, chlorins, bacteriochlorins, phthalocyanines, porphyrins, purpurins, merocyanines, psoralens, benzoporphyrin derivatives (BPD), and porfimer sodium and pro-drugs such as delta-aminolevulinic acid, which can produce photosensitive agents such as protoporphyrin IX. Other suitable photosensitive compounds include ICG, methylene blue, toluidine blue, texaphyrins, and any other agent that absorbs light in a range of 500 nm–1100 nm.

The term "preferentially associates" or "preferential association" is used herein to describe the preferential association between a photosensitizing agent and target tissue, such as tumor cells or tumor tissue. More specifically, the present invention provides for the photodynamic therapy of a mammalian subject, where the preferential association by photosensitizing agents for target tissue, including tumor cells or tumor tissues, results in the destruction or damage to target tissue upon irradiation. The surrounding normal or healthy tissue is not damaged, where the photosensitizing agent clears much more rapidly from normal cells or tissues than it does from target tissue.

"Inert" is used herein as meaning not manifesting biologically and/or chemically therapeutic or detrimental properties but having the potential to manifest such properties upon exposure to the appropriate wavelength or waveband energy source. The fact that an inert photosensitizer agent or ligand-receptor binding pair conjugate is selectively absorbed by, or preferentially associated with, targeted cells is not meant to affect this interpretation.

The term "prodrug" is used herein to mean any of a class of substances that are not themselves photosensitive agents, but when introduced into the body, through metabolic, chemical, or physical processes, are converted into a photosensitive agent. In the following disclosure, an aminolevulinic acid (ALA) is the only exemplary prodrug. After being administered to a patient ALA is metabolically converted into a porphyrin compound that is an effective photosensitive agent.

"Radiation" as used herein includes all wavelengths and wavebands. Preferably, the radiation wavelength or waveband is selected to correspond with or at least overlap the wavelength(s) or wavebands that excite the photosensitive compound. Photosensitive agents or compound typically have one or more absorption wavebands that excite them to produce the substances, which damage or destroy target tissue, target cells, or target compositions. Even more preferably, the radiation wavelength or waveband matches the excitation wavelength or waveband of the photosensitive compound and has low absorption by the non-target cells and the rest of the intact animal, including blood proteins. For example, a preferred wavelength of light for ICG is in the range 750–850 nm.

The radiation used to activate the photosensitive compound is further defined in this invention by its intensity, duration, and timing with respect to dosing a target site. The intensity or fluence rate must be sufficient for the radiation to penetrate skin and reach the target cells, target tissues, or target compositions. The duration or total fluence dose must be sufficient to photoactivate enough photosensitive agent to achieve the desired effect on the target site. Both intensity and duration are preferably limited to avoid over treating the subject or animal. Timing with respect to the dosage of the photosensitive agent employed is important, because (1) the administered photosensitive agent requires some time to home in on target cells, tissue, or compositions at the treatment site, and (2) the blood level of many photosensitive agents decreases with time.

The present invention provides a method for providing a medical therapy to an animal, and the term "animal" includes, but is not limited to, humans and other mammals. The term "mammals" or "mammalian subject" includes farm animals, such as cows, hogs and sheep, as well as pet or sport animals such as horses, dogs, and cats.

Reference herein to "intact animal" means that the whole, undivided animal is available to be exposed to radiation. No part of the animal is removed for exposure to the radiation, in contrast with photophoresis, in which an animal's blood is circulated outside its body for exposure to radiation. However, in the present invention, the entire animal need not be exposed to radiation. Only a portion of the intact animal subject may or need be exposed to radiation, sufficient to ensure that the radiation is administered to the treatment site where the target tissue, cells, or compositions are disposed.

In the present invention, a photosensitizing agent is generally administered to the animal before the animal is subjected to radiation. Preferred photosensitizing agents include, but are not limited to, chlorins, bacteriochlorins, phthalocyanines, porphyrins, purpurins, merocyanines, psoralens and pro-drugs such as δ-aminolevulinic acid, which can produce drugs such as protoporphyrin. More preferred photosensitizing agents are: methylene blue, toluidine blue, texaphyrins, and any other agent that absorbs light having a wavelength or waveband in the range from 600 nm–100 nm. Most preferred of the photosensitizing agents is ICG. The photosensitizing agent is preferably administered locally or systemically, by oral ingestion, or by injection, which may be intravascular, subcutaneous, intramuscular, intraperitoneal or directly into a treatment site, such as intratumoral. The photosensitizing agent can also be administered internally or topically via patches or implants.

The photosensitizing agent also can be conjugated to specific ligands known to be reactive with a target tissue, cell, or composition, such as receptor-specific ligands or immunoglobulins or immunospecific portions of immunoglobulins, permitting them to be more concentrated in a desired target cell or microorganism than in non-target tissue or cells. The photosensitizing agent may be further conjugated to a ligand-receptor binding pair. Examples of a suitable binding pair include but are not limited to: biotin-streptavidin, chemokine-chemokine receptor, growth factor-growth factor receptor, and antigen-antibody. As used herein, the term "photosensitizing agent delivery system" refers to a photosensitizing agent conjugate, which because of its conjugation, has increased selectivity in binding to a target tissue, target cells, or target composition. The use of a photosensitizing agent delivery system is expected to reduce the required dose level of the conjugated photosensitizing agent, since the conjugate material is more selectively targeted at the desired tissue, cell, or composition, and less of it is wasted by distribution into other tissues whose destruction should be avoided.

Figure 3A:
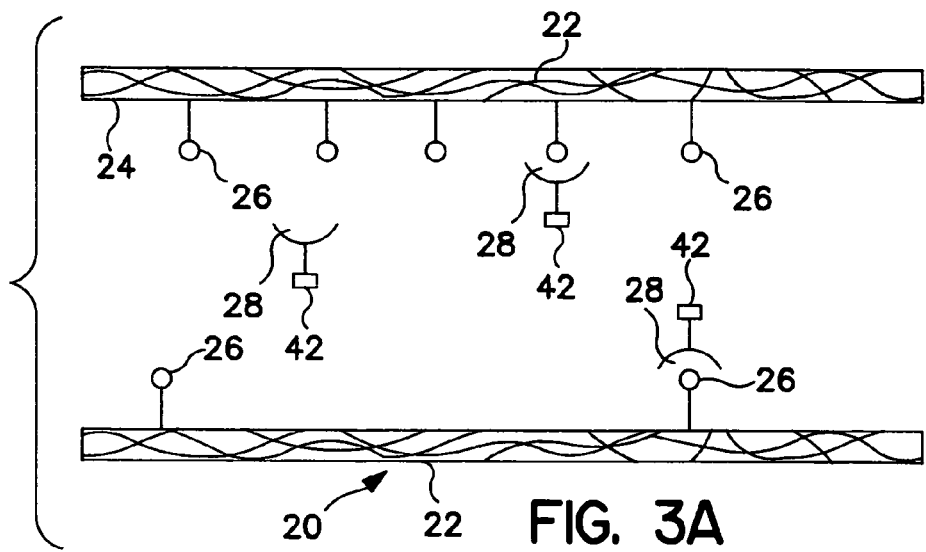
FIGS. 3A and 3B are schematic diagrams illustrating biotin-avidin targeting of endothelial antigens for use in rendering PDT.
Figure 3B:
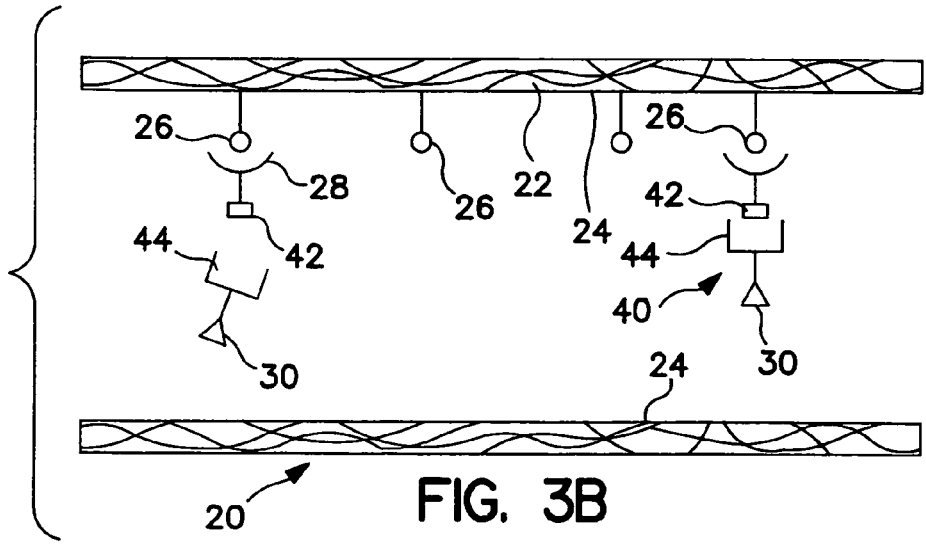

In FIGS. 3A and 3B, an example of a photosensitizing agent delivery system 40 is illustrated in which the target tissue is endothelial layer 24, which is disposed along blood vessel wall 22 of tumor blood vessel 20. As shown in FIG. 3A, antibodies 28 are coupled with biotin molecules 42 and thus selectively linked to endothelial antigens 26 along the endothelial layer. FIG. 3B illustrates avidin molecules 44 coupled to PDT photosensitive drug molecules 30, where the avidin molecules bind with biotin molecules 42. This system thus ensures that the PDT photosensitive drug molecules 30 only link with the selectively targeted endothelial tissue. When light of the appropriate waveband is administered, it activates the PDT photosensitive drug molecules, causing the endothelial tissue to be destroyed.

Figure 4A:
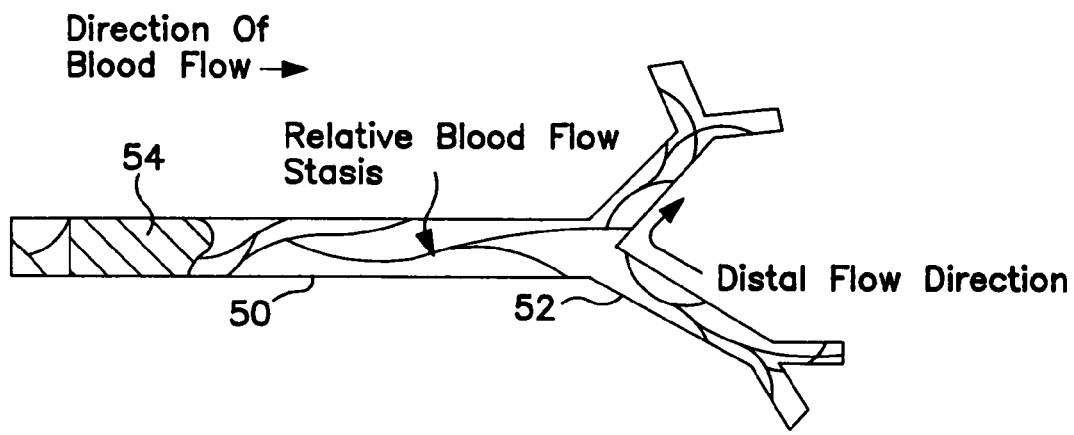
FIGS. 4A–4C schematically illustrate tissue amplified infarction downstream of photodynamic transcutaneous therapy applied to endothelium tissue.
Figure 4B:
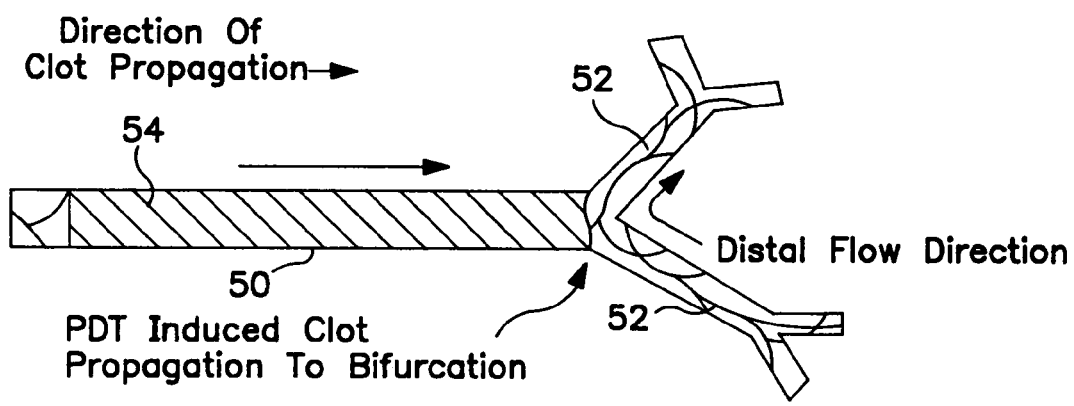
Figure 4C:
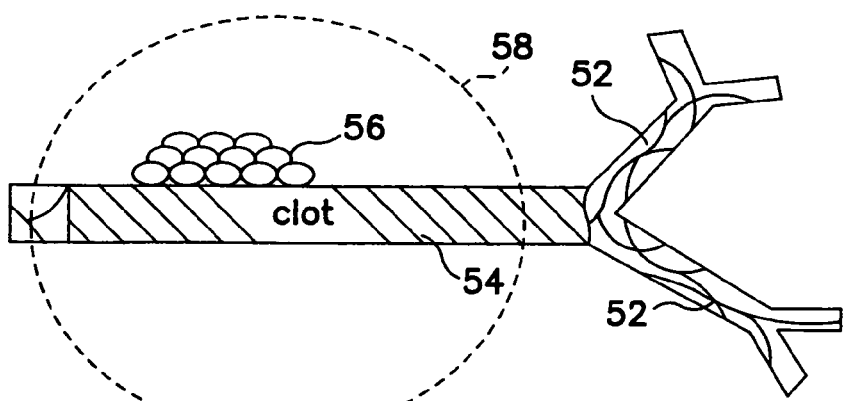

FIGS. 4A–4C illustrate a mechanism for amplifying the effect on a tumor of PDT administered to destroy the endothelial tissue in a tumor blood vessel 50. Tumor blood vessel 50 distally branches into two smaller blood vessels 52. In FIG. 4A, the PDT administered to activate the PDT photosensitive drug molecules has produced substantial damage to the endothelium, creating an intravascular thrombosis (or clot) 54. As shown in FIG. 4B, the intravascular thrombosis is carried distally through tumor blood vessels 50 until it reaches the bifurcation point where smaller diameter blood vessels 52 branch. Due to the flow through smaller internal diameter of blood vessels 52, intravascular thrombosis 54 can not advance any further, and is stopped, creating a plug that virtually stops blood flow through tumor blood vessel 50. FIG. 4C, the interruption of blood flow also interrupts the provision of nutrients and oxygen to the surrounding tumor cells, causing the tumor cells to die. The dying tumor cells 56 are within a zone of tumor cell death or necrosis 58 surrounding the vessel and which zone increases in volume over time, thereby amplifying the effects of the PDT on the endothelium tissue of the tumor blood vessels.

A photosensitizing agent can be administered in a dry formulation, such as pills, capsules, suppositories or patches. The photosensitizing agent also may be administered in a liquid formulation, either alone, with water, or with pharmaceutically acceptable excipients, such as are disclosed in Remington's Pharmaceutical Sciences. The liquid formulation also can be a suspension or an emulsion. In particular, liposomal or lipophilic formulations are desirable. If suspensions or emulsions are utilized, suitable excipients include water, saline, dextrose, glycerol, and the like. These compositions may contain minor amounts of nontoxic auxiliary substances such as wetting or emulsifying agents, antioxidants, pH buffering agents, and the like.

The dose of photosensitizing agent will vary with the target tissue, cells, or composition, the optimal blood level (see Example 1), the animal's weight, and the timing and duration of the radiation administered. Depending on the photosensitizing agent used, an equivalent optimal therapeutic level will have to be empirically established. Preferably, the dose will be calculated to obtain a desired blood level of the photosensitizing agent, which will likely be between about 0.01 µg/ml and 100 µg/ml. More preferably, the dose will produce a blood level of the photosensitizing agent between about 0.01 µg/ml and 10 µg/ml.

The intensity of radiation used to treat the target cell or target tissue is preferably between about 5 mW/cm$^2$ and about 500 mW/cm$^2$. More preferably, the intensity of radiation employed should be between about 10 mW/cm$^2$ and about 100 mW/cm$^2$. Most preferably, the intensity of radiation is between about 15 mW/cm$^2$ and about 50 mW/cm$^2$.

The duration of radiation exposure administered to a subject is preferably between about 4 minutes and 72 hours. More preferably, the duration of radiation exposure is between about 60 minutes and about 48 hours. Most preferably, the duration of radiation exposure is between about 2 hours and about 24 hours.

The intensity or power of the light used is measured in watts, with each Joule equal to one watt-sec. Therefore, the intensity of the light used for irradiating in the present invention may be substantially less than 500 mW/cm$^2$. Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The present invention employs an amount of total fluence of irradiation that is sufficiently high to activate the photosensitizing agent, as applicable, with a concomitant reduction in the intensity of light and collateral or non-target specific tissue damage.

The present invention provides that an optimal total fluence for the light administered to a subject will be determined clinically, using a light dose escalation trial. It is further contemplated that the total fluence administered during a treatment will preferably be in the range of 30 Joules to 25,000 Joules, more preferably, in the range from 100 Joules to 20,000 Joules, and most preferably, in the range from 500 Joules to 10,000 Joules.

It is contemplated that a targeted photosensitizer agent can be substantially and selectively photoactivated in the target cells and target tissues within a therapeutically reasonable period of time and without excess toxicity or collateral damage to non-target normal tissues. Thus, there appears to be a therapeutic window bounded by the targeted photosensitizer agent dosage and the radiation dosage. In view of problems in the prior art related to either extracorporeal treatment of target tissues or use of high intensity laser light irradiation intra-operatively, the present invention offers substantial advantages. In accord with the present invention, targeted transcutaneous PDT will be employed to treat patients injected with a photosensitizer agent and will subject the patients to a relatively low fluence rate, but high total fluence dose of radiation. This approach is an attractive method for treating target tissues that include neoplastic diseased tissue, infectious agents, and other pathological tissues, cells, and compositions.

One aspect of the present invention is drawn to a method for transcutaneous energy activation therapy applied to destroy tumors in a mammalian subject or patient by first administering to the subject a therapeutically effective amount of a first conjugate comprising a first member of a ligand-receptor binding pair conjugated to an antibody or antibody fragment. The antibody or antibody fragment selectively binds to a target tissue antigen. Simultaneously or subsequently, a therapeutically effective amount of a second conjugate comprising a second member of the ligand-receptor binding pair conjugated to an energy-sensitive agent or energy-sensitive agent delivery system for prodrug is administered to the patient, wherein the first member binds to the second member of the ligand-receptor binding pair. These steps are followed by irradiating at least a portion of the subject with energy having a wavelength or waveband absorbed by the energy-sensitive agent, or energy-sensitive agent delivery system, or by the product thereof. This radiation energy is preferably provided by an energy source that is external to the subject and is preferably administered at a relatively low fluence rate that results in the activation of the energy-sensitive agent, or energy-sensitive delivery system, or prodrug product.

While one preferred embodiment of the present invention is drawn to the use of light energy for administering PDT to destroy tumors, other forms of energy are within the scope of this invention, as will be understood by those of ordinary skill in the art. Such forms of energy include, but are not limited to: thermal, sonic, ultrasonic, chemical, light, microwave, ionizing (such as x-ray and gamma ray), mechanical and electrical. For example, sonodynamically induced or activated agents include, but are not limited to: gallium-porphyrin complex (see Yumita et al., *Cancer Letters* 112: 79–86, (1997)), other porphyrin complexes, such as protoporphyrin and hematoporphyrin (see Umemura et al., *Ultrasonics Sonochemistry* 3:S187–S191, (1996)); other cancer drugs, such as daunorubicin and adriamycin, used in the presence of ultrasound therapy (see Yumita et al., *Japan J. Hyperthermic Oncology* 3(2):175–182, (1987)).

Figure 5:
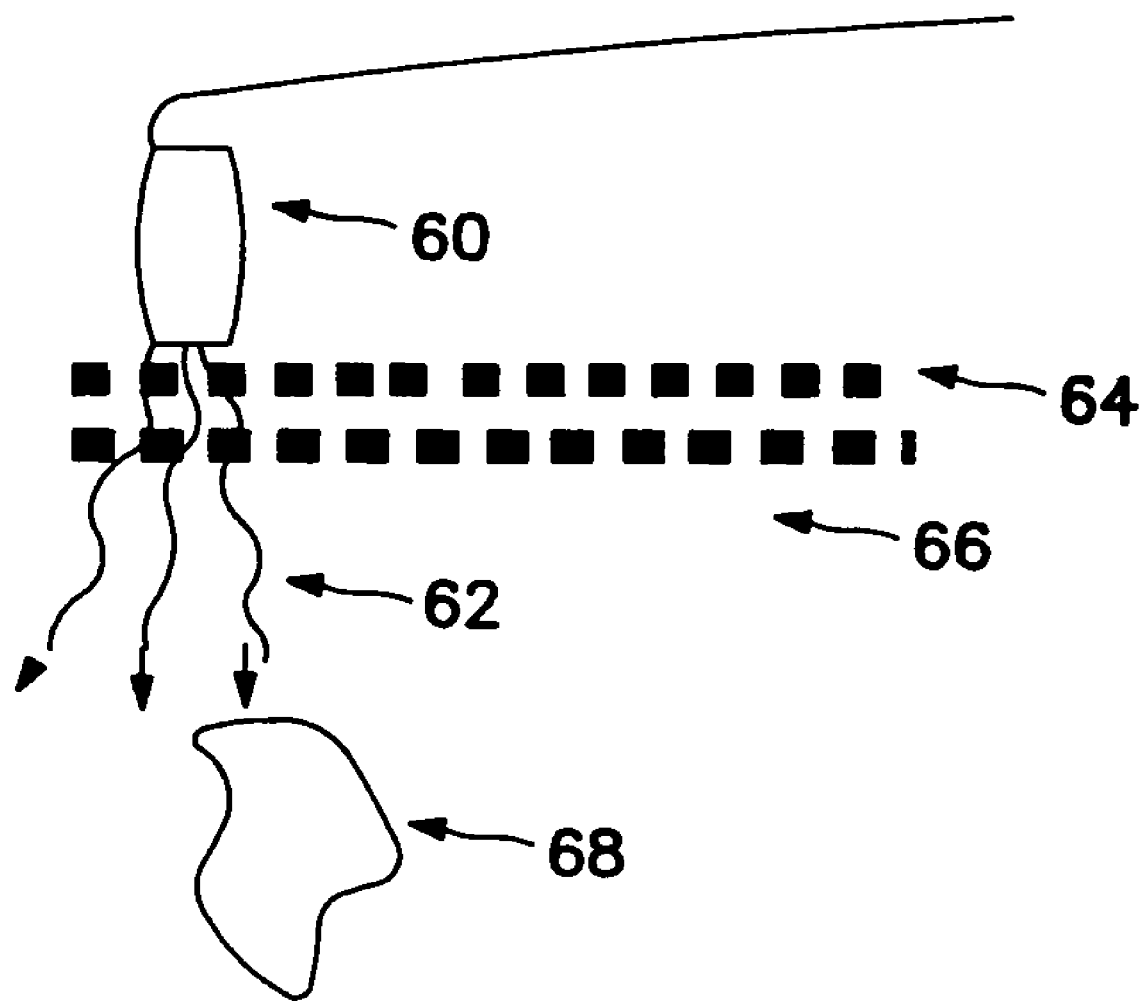
FIG. 5 is a schematic diagram illustrating the use of an external ultrasound source for transcutaneous application of PDT to a deep tumor.

FIG. 5 illustrates the use of an external ultrasound transducer head 60 for generating an ultrasonic beam 62 that penetrates through a dermal layer 64 and into a subcutaneous layer 66. The external ultrasound transducer head is brought into contact with dermal layer 64 so that ultrasonic beam 62 is directed toward a relatively deep tumor 68. The ultrasonic beam activates a PDT photosensitive drug that has been administered to the patient and selectively targeted at tumor 68, causing the drug to destroy the tumor.

This invention further preferably employs an energy source, e.g., a light source, that is external to the target tissue. The target tissues may include and may relate to the vasculature or blood vessels that supply blood to tumor tissue or the target tissues may include the tumor tissue antigens, per se. These target tissue antigens will be readily understood by one of ordinary skill in the art to include but to not be limited to: tumor surface antigen, tumor endothelial antigen, non-tumor endothelial antigen, and tumor vessel wall antigen, or other antigens of blood vessels that supply blood to the tumor.

Where the target tissue includes endothelial or vascular tissue, a preferable ligand-receptor binding pair includes biotin-streptavidin. In this preferred embodiment, the activation of photosensitizer agents by a relatively low fluence rate of a light source over a prolonged period of time results in the direct or indirect destruction, impairment or occlusion of blood supply to the tumor resulting in hypoxia or anoxia to the tumor tissues. Where the target tissue includes tumor tissue other than endothelial or vascular, the activation of photosensitizer agents by a relatively low fluence rate of a light source over a prolonged period of time results in the direct destruction of the tumor tissue due to the deprivation of oxygen and nutrients from the tumor cells.

The ordinary skilled artisan would be familiar with various ligand-receptor binding pairs, including those known and those currently yet to be discovered. Those known include, but are not limited to: biotin-streptavidin, chemokine-chemokine receptor, growth factor-growth factor receptor, and antigen-antibody. The present invention contemplates at least one preferred embodiment that uses biotin-streptavidin as the ligand-receptor binding pair. However, the ordinary skilled artisan will readily understand from the present disclosure that any ligand-receptor binding pair may be useful in practicing this invention, provided that the ligand-receptor binding pair demonstrates a specificity for the binding by the ligand to the receptor and further provided that the ligand-receptor binding pair permits the creation of a first conjugate comprising a first member of the ligand-receptor pair conjugated to an antibody or antibody fragment. In this case, the antibody or antibody fragment selectively binds to a target tissue antigen and permits the creation of a second conjugate comprising a second member of the ligand-receptor binding pair conjugated to an energy-sensitive or photosensitizing agent, or energy-sensitive or photosensitizing agent delivery system, or prodrug. The first member then binds to the second member of the ligand-receptor binding pair.

Another preferred embodiment of the present invention includes a photosensitizing agent delivery system that utilizes both a liposome delivery system and a photosensitizing agent, where each is separately conjugated to a second member of the ligand-receptor binding pair, and where the first member binds to the second member of the ligand-receptor binding pair. More preferably, the ligand-receptor binding pair is biotin-streptavidin. In this embodiment, the photosensitizing agent as well as the photosensitizing agent delivery system may both be specifically targeted through selective binding to a target tissue antigen by the antibody or antibody fragment of the first member binding pair. Such dual targeting is expected to enhance the specificity of uptake and to increase the quantity of uptake of the photosensitizing agent by the target tissue, cell, or compositions.

In a more preferred embodiment of the invention, a photosensitizer compound is used that clears the normal tissue of the skin in a short amount of time and is retained in the targeted tissue for a relatively longer period of time. Examples of such photosensitizer compounds include Lutrin™ (lutetium texaphyrin, brand; Pharmacyclics, Inc, Sunnyvale, Calif.) and bacterio-chlorophylls. Preferably the waiting time for the photosensitizer compound to clear the normal tissue and skin is about 24 hours. The exact dosage of such a photosensitizer compound will depend upon the compound and its pharmacokinetics, but generally such dosages can be routinely determined clinically and will be the lowest dose that saturates the available binding sites. Depending on the photosensitizing compound used, an equivalent optimal therapeutic level will have to be established.

Such photosensitizer compounds are to be administered in any therapeutically effective manner, preferably intravenously and at a dosage of from about 0.05 to about 100 mg/kg. Alternatively, the dosage may be determined as about 0.15 to about 50.0 mg/m$^2$. More preferably, such dosage is from about 1.0 to 50 mg/kg or about 5 to about 30 mg/m$^2$.

After the drug has cleared the normal tissues, it is retained in the target tissue, such as a tumor, a light source is positioned above the site to be treated. Any suitable light source can be used, such as LED array, laser diode array, or any other type of electroluminescent device such as a light emitting flat panel which can be flexible or nonflexible. After the light emitting device is energized, the light is transmitted noninvasively through the skin and intravening tissues to the treatment site. The length of time of treatment may be optimized in a clinical trial using standard clinical practice and procedures. It is expected that at least one hour of treatment will be necessary to ensure that an adequate number of photochemical reactions occurs in order to completely destroy the target tissue so that cellular repair is not feasible. The targeted tissue, which has selectively taken up the photosensitizer compound, is destroyed during the light activation or PDT process. Unlike radiotherapy and chemotherapy, there is less dose limitation of the drug or the light and thus the process can be repeated as necessary if new tumor tissues develop.

Although light is delivered through normal tissue, there is little, if any, collateral damage to normal tissue because the drug is taken up selectively and the PDT effect only occurs where drug uptake has taken place. A unique aspect of this methodology is that each drug molecule can be repeatedly activated causing a drug amplification effect. The drug amplification effect allows a relatively low dose of drug to be highly effective in terms of singlet oxygen generation by the photoactivation process. Notably, whether it is the singlet oxygen generated from the PDT activation of the drug which destroys the tumor cells or an immune response stimulated by PDT tumor tissue damage or both, there is little damage to the tissue from the drug itself.

Having now generally described the invention, it will be more readily understood through reference to the following examples, which are provided by way of illustration and are not intended to be limiting in regard to the scope of the invention, unless specified.

EXAMPLES

Example 1

Transcutaneous Photodynamic Therapy of a Solid Type Tumor

A patient in the terminal phase of recurrent malignant colon cancer having undergone chemotherapy and irradiation therapy, presented with a protruding colon carcinoma tumor mass of approximately 500 grams and approximately 13 cm in diameter, which extended through the patient's dermis. Due to the advanced state of the patient's disease and due to the highly vascularized nature of this tumor mass, resection was not feasible. Further, this large tumor mass presented a significant amount of pain and discomfort to the patient, as well as greatly impairing the patient's ability to lie flat.

Six separate light source probes, each including a linear array of LEDs, were surgically implanted in this large tumor using standard surgical procedures. A single dose of a photosensitizer agent (aminolevulinic acid (ALA) at 60 mg/kg) was provided by oral administration to the patient. Following a period of five hours to permit sufficient clearance of the photosensitizing agent from healthy tissues, light irradiation was administered. An intensity of about 25–30 mW of light from each light source probe (650 nm peak wavelength) was delivered to the tumor for 40 hours. However, after 18 hours, two of the light source probes became unseated from the tumor mass and were disconnected from the electrical power supply used to energize the LEDs on each probe. The total fluence delivered to the tumor bed during this single extended duration treatment was in excess of 20,000 Joules.

Extensive tumor necrosis in a radius of greater than about 5 cm from each of the light source probes was observed after 40 hours of PDT, with no collateral damage to surrounding normal tissue. The extent of this PDT induced necrotic effect in a large volume of tumor tissue was totally unexpected and has not been described before in any PDT studies in subjects in vivo or clinically. Over the course of four weeks following PDT, the necrotic tumor tissue was debrided from the patient resulting in a reduction of approximately 500 grams of tumor tissue. The patient noted a significant improvement in his quality of life, with a resurgent level of energy and improved well being.

The average thickness of human skin is approximately 1 cm. Therefore, if this same method of prolonged, relatively low fluence rate, but overall high total fluence of light delivery is utilized to deliver the light transcutaneously, a therapeutic effect well below the skin surface, to a depth of greater than about 5 cm is contemplated.

The fluence rate employed in this Example represented about 150–180 mW/cm$^2$, with a total fluence more than 20,000 Joules. The preferable fluence rate contemplated more broadly by the present invention is between about 5 mW/cm$^2$ and about 100 mW/cm$^2$, more preferably, between about 10 mW/cm$^2$ and about 75 mW/cm$^2$, and most preferably, between about 15 mW/cm$^2$ and about 50 mW/cm$^2$.

It is further contemplated that the optimal fluence be empirically determined, using a light dose escalation trial, and will likely and preferably be in the range of about 30 Joules to about 25,000 Joules, and more preferably be in the range from about 100 Joules to about 20,000 Joules, and most preferably be in the range from about 500 Joules to about 10,000 Joules.

Example 2

Transcutaneous Photodynamic Therapy of Intraosseous Disease

The current accepted therapy for treating leukemia and other malignant bone marrow diseases employs a systemic treatment utilizing chemotherapy and/or radiotherapy, sometimes followed by a bone marrow transplant. There are significant risks associated with non-discriminative ablative therapies that destroy all marrow elements, including the risks of infections, bleeding diathesis, and other hematological problems.

There is a definite need for alternative therapies that do not subject patients to procedures which may be risky and which inherently cause pain and suffering. This example is directed to a method of treating intraosseous malignancy that has major advantages over the prior art techniques for treating this disease.

A targeted antibody-photosensitizer conjugate (APC) is constructed, which binds selectively to antigens present on leukemic cells. This ligand-receptor binding pair or APC is infused intravenously and is taken up in the marrow by circulating leukemic cells, and by stationary deposits and may reside in other organs. When unbound to leukemic cells, APC is eliminated from the body. Internal or external light sources may be used to activate the targeted drug. For example, light bar probes disclosed in U.S. Pat. No. 5,445,608 may be inserted into bone marrow to treat the intraosseous disease. The devices disclosed in U.S. Pat. No. 5,702,432 may be used to treat disease cells circulating in the patient's lymphatic or vascular system. An external device transcutaneously activating the targeted drug, for example, a light source that emits light that is transmitted through the dermal layer may also be used in treating the marrow compartment in accord with the present invention.

PDT targeting has been described for leukemic cells (see U.S. Pat. No. 5,736,563) but not with capability of treating marrow in situ. Without this capability, simply lowering the leukemic cell count would have little clinical benefit, since the marrow is a major source of new leukemic clones, and the marrow must be protected from failure, which will lead to the death of the patient regardless of how well the pathologic cell load in the circulation is treated. Specific APC promotes the selective damage of leukemic cells in marrow, while reducing collateral and non-target tissue damage. Further, the use of a relatively low fluence rate, but overall high total fluence dose is particularly effective in this therapy. Optimal fluence rates and dosing times are readily empirically determined using dose escalation for both drug and light dose as is often done in a clinical trial. Any of a number of different types of leukemia cell antigens may be selected, provided that the antigen chosen is as specific as possible for the leukemia cell. Such antigens will be known to those of ordinary skill in this art. The selection of a specific photosensitizer agent may be made, provided that the photosensitizer agent chosen is activated by light having a waveband of from about 500 nm to about 1100 nm, and more preferably, a waveband from about 630 nm to about 1000 nm, and most preferably, a waveband from about 800 nm to about 950 nm or greater. The photosensitizer agents noted above are suitable for use in this Example.

Figure 6:
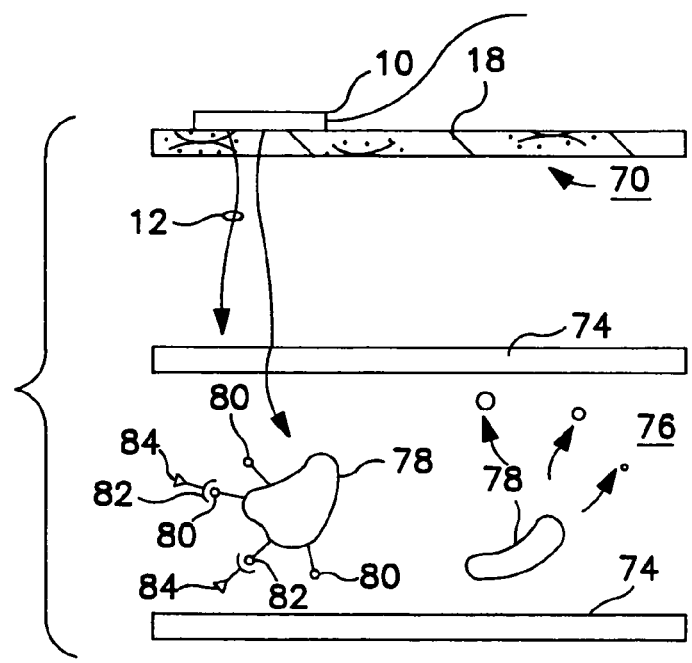
FIG. 6 is a schematic diagram showing the use of an external light source for transcutaneous treatment of intraosseous disease.

With reference to FIG. 6, external light source 10 is administering light 12 transcutaneously through dermal layer 18. Light 12 has a sufficiently long wavelength to pass through a subcutaneous layer 70 and through a cortical bone surface 74, into a bone marrow compartment 76. Leukemia cells 78 have penetrated bone marrow compartment 76 and are distributed about within it. To provide targeted PDT treatment that will destroy the leukemia cells, antibodies 82 linked with PDT photosensitive drug molecules 84 have been administered to the patient and have coupled with leukemia antigens 80 on the leukemia cells 78. The light provided by external light source 10 thus activates the PDT photosensitive drug, causing it to destroy the leukemia cells. This targeted PDT process is carried out with minimal invasive or adverse impact on the patient, in contrast to the more conventional treatment paradigms currently used.

Example 3

Transcutaneous Photodynamic Therapy of Crohn's Disease

Figure 7:
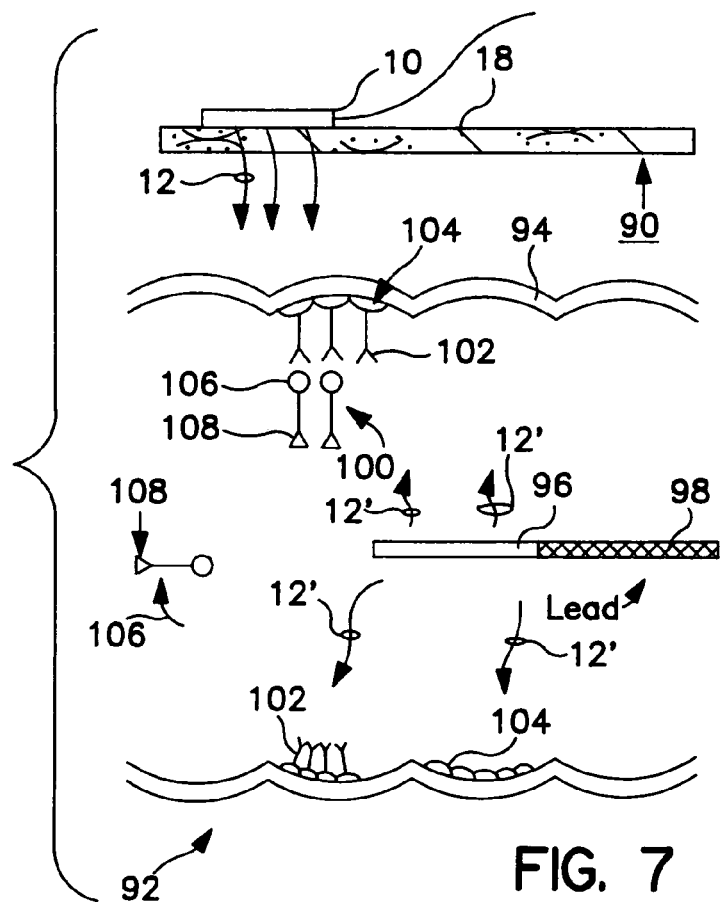
FIG. 7 is a schematic diagram showing both an external light source transcutaneously administering light and an intraluminal light source position within either the terminal ileum or colon to treat Crohn's disease with targeted PDT.

Crohn's disease is a chronic inflammation of the gastrointestinal tract thought to be mediated in large part by dysfunction of $CD4^+$ T cells lining the gut mucosa, especially in the terminal ileum. The current accepted therapy for Crohn's disease provides for surgical removal of the inflamed bowel segment and the use of anti-inflammatory agents, steroids and other immunosuppressive drugs. None of these measures is entirely satisfactory due to surgical risk, recurrence of disease, medication side effects, and refractoriness of the disease. There is a clear need for alternative therapies useful in treating this immune dysfunction that offer greater efficacy and reduced side effects and risk. This Example, details of which are illustrated in FIG. 7, indicates the drug compositions and methodologies useful in accord with the present invention to selectively destroy the dysfunctional cells or inhibit their function. In the illustrated example, external light source 10 is administering light 12 that has a sufficiently long wavelength to penetrate dermal tissue 18, which is disposed over a patient's abdomen, and pass through a subcutaneous layer 90, into a terminal ileum or colon 92. The light passes through wall 94 of the terminal ileum or colon. Alternatively (or in addition), light 12' can be administered from an intraluminal probe 96, from sources (not separately shown) that are energized with an electrical current supplied through a lead 98.

Ligand-receptor binding pairs 100, or more specifically, APCs, are created that bind selectively to $CD4^+$ T cell antigens 102 of T cells 104, which are disposed along the interior, intraluminal surface of the terminal ileum or colon. For example, the $CD4^+$ antigen itself may be targeted by those antibodies 106 that bind specifically to the $CD4^+$ antigen. Many of the photosensitizer agents noted above may be used for photosensitizing drug molecules 108, in the therapy of this Example. The APC is preferably formulated into a pharmaceutically acceptable compound that can be released in the terminal ileum and colon in a manner similar to that known to be used for the orally delivered form of Budesonide™ also known as Entocort™. The APC compound is ingested and releases the conjugate into the terminal ileum and colon. At the time of therapy, the bowel should have been prepped in much the same manner as done in preparing for a colonoscopy, so that it is cleared of fecal material. The targeted photosensitizer will bind to the pathologic T cells and any unbound APC is removed via peristaltic action. The sensitizer bound to the T cells is activated by intraluminally positioned light source probe 96, details of which are disclosed in any one of U.S. Pat. Nos.: 5,766,234; 5,782,896; 5,800,478; and 5,827,186, each of which is hereby incorporated by reference herein in its entirety; or by a flexible intraluminal optical fiber (not shown) that is passed via the nasopharynx; or, by the transcutaneous light illumination provided by external light source 10. Transcutaneous light illumination is preferred because it is entirely noninvasive.

In this example treatment, the following protocol may be utilized:

Step 1 Patient is NPO ("non per os" or nothing by mouth) and the bowel has been prepped or cleansed by administering an enema to clear it of fecal material;

Step 2 Specially formulated APC conjugate compound 100 is ingested;

Step 3 The APC conjugate is released to the terminal ileum and colon;

Step 4 If transcutaneous illumination is not used, one or more light source probes 96 are ingested or passed into the GI tract and advanced to the terminal ileum or colon.

Step 5 The APC conjugate is bound to target T cells 104 and any unbound conjugate fraction passes distally via peristalsis (and is subsequently eliminated from the body).

Step 6 If an internal light source is used, the light source should preferably be imaged using ultrasound or computer assisted topography (i.e., a CT scan—not shown) to confirm its location and the light source can then be activated while positioned in the ileum. Once activated, the light source will deliver light at the appropriate waveband for the photosensitizing agent selected, at a relatively low fluence rate, but at a high total fluence dose, as noted above. The optimal drug dose and fluence parameters will be determined clinically in a drug and light dose escalation trial. The light dose and drug dose are such that T cell inactivation occurs, leading to decreased regulation of the immune process and a reduction of any pathologic inflammation—both of which are factors characteristic of this disease.

Step 7 The light source is deactivated. It is particularly important to deactivate an internal light source before withdrawing it from the treatment site to prevent nonspecific APC activation.

The present invention can also be employed to target other types of immunologic cells, such as other T cells, macrophages, neutrophils, B cells, and monocytes. A tiered approach can thus be employed, starting with CD4$^+$ T cells, then moving to CD8$^+$ T cells, and then monocytes, and neutrophils. By inhibiting or preventing interaction and/or secretion of inflammatory cell products, the pathologic process is controlled at the lumenal site, completely avoiding systemic side effects and major surgery. The same process can be applied to treat ulcerative colitis with the same benefits. As indicated above, the APC can be activated with light administered transcutaneously, using any number of different types of external light sources such as LEDs, laser diodes, and lamps that emit light with a wavelength or waveband sufficiently long to penetrate through the overlying dermal and internal tissue, and into the intestine. The optical wavelength or waveband of this light is determined by both the light absorption properties of the photosensitizer and the need to use light with as long a wavelength as possible to ensure adequate penetration into the patient's body. A desirable photosensitizer is preferably one that absorbs in the range from about 700 nm to about 900 nm, which optimizes tissue penetration. The appropriate fluence rate and total fluence delivered is readily determined by a light dose escalation clinical trial. The light dose and drug dose are such that T cell inactivation occurs, leading to reduced regulation of the immune process and a reduction in pathologic inflammation.

Example 4

Intraluminal/Transcutaneous PDT Targeted at *Helicobacter pylori*

Figure 8:
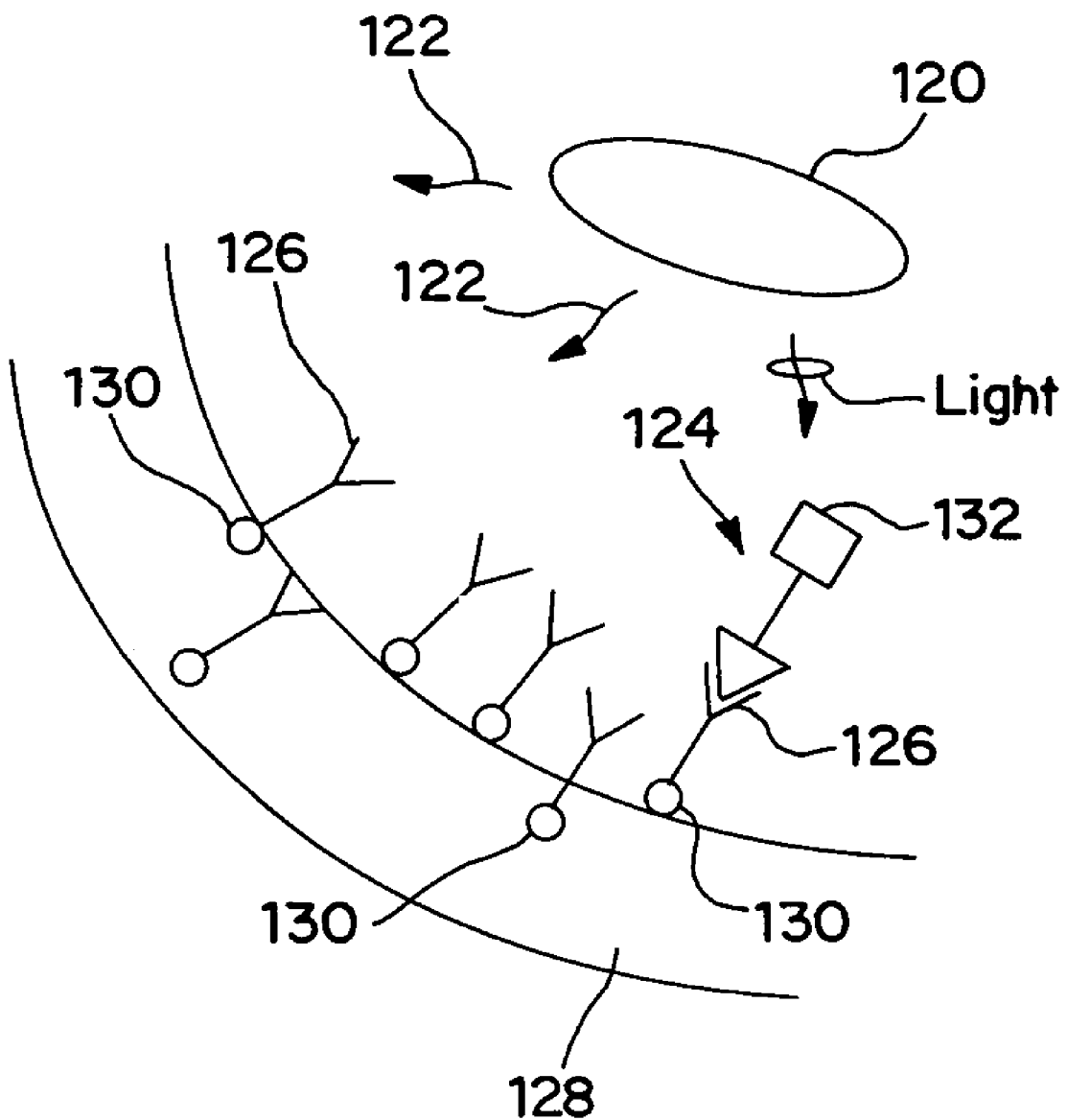
FIG. 8 is a schematic diagram illustrating an intraluminal light source in the form of a capsule or pill for administering light to destroy *H. pylori* on the gastric lining with targeted PDT.

While there has been research relating to the targeting of photosensitizers to bacterial cells, it is not apparent from the prior art whether such research is useful in a clinical setting or to destroy and/or impair target cells. Many antigens that can serve as targets for ligand-receptor binding pairs, and more specifically, APC, have been identified, and the techniques to construct such conjugates are well within the ordinary skill in this art. It is also not apparent from the prior art what steps or in what manner such steps are necessary to apply such conjugates in the treatment of a clinical disease. This Example describes the clinical application of APC to the treatment of an infection using PDT. FIG. 8 illustrates details of the example, as described below. Further, this Example provides helpful guidance for a noninvasive or minimally invasive method using PDT. This is a transcutaneous method of treatment because no incision is required and the subject body is intact. Instead, the light source is introduced into a naturally formed passage of the subject.

*Helicobacter pylon* is reportedly associated with tumors of the stomach in mice and as a putative agent of ulcerative pathology in humans. Proposals have been described to employ laser light as disclosed by Wilder-Smith et al. (*AGA Abstracts: Gastroenterology*, 116(4), A354, 1999) for treating infection by *H. pylori* in human patients as well as infection by other bacteria (Millson et al, *J. of Photochemistry and Photobiology* 32: 59–65 (1996)). However, the use of laser light necessarily involves the use of high intensity irradiation for a short period of time, frequently resulting in undesirable collateral tissue damage.

In this Example, a capsular or pill-shaped and sized light source 120 is administered orally to a patient, so that it passes into the stomach 118 of the patient, where it administers light 122. Alternatively, an optical fiber (not shown) may be passed into the stomach via the nasopharynx to administer light 122 to the treatment site. In order to implement targeted PDT for treating ulcers in humans, and APC 124, with antibody 131 is targeted against a suitable *Helicobacter pylori* antigen 126. The APC is formulated into an ingestible compound that releases the APC to a gastric mucus/epithelial layer 128 where the bacterium is found. The APC is ingested at a time when the stomach and duodenum is substantially empty in order to promote binding of the APC to bacterium 130. Any unbound APC is diluted by gastric juice and carried distally by peristalsis to be eliminated from the body in fecal matter. Light sources suitable for intraluminal passage are disclosed in any one of U.S. Pat. Nos.: 5,766,234; 5,782,896; 5,800,478; and 5,827,186, the disclosure of each being specifically hereby incorporated herein in its entirety.

Alternatively, light source 120 in capsule or pill form, e.g., as disclosed in copending commonly assigned U.S. patent application Ser. No. 09/260,923, entitled, "Polymer Battery for Internal Light Device," filed on Mar. 2, 1999 and which is hereby incorporated in its entirety by reference herein, is used for activating the APC. The light source is preferably energized just prior to its ingestion or remotely after ingestion, when in the stomach or in a desired intraluminal passage. If necessary, multiple light sources are ingested to insure that adequate photoactivation of the localized APC occurs sufficient to kill the bacterium. Light is delivered at a relatively low fluence rate but at a high total fluence dose, as discussed above. The light source(s) may be deactivated after passage beyond the duodenum to avoid unwanted distal photoactivation. In this manner, a photosensitizing agent 132 comprising the APC is activated topically without the need for a procedure such as endoscopy with fiberoptic gastric illumination in order to provide the activating light. Since the APC is targeted, nonspecific uptake by normal tissue and other normal compositions of the body is minimized in order to prevent injury to normal gastric tissue and problems with the gastric system.

In this exemplary treatment, the following protocol may be utilized:

Step 1 Patient is NPO for six hours to insure that the stomach is empty.

Step 2 The APC is ingested.

Step 3 One hour elapses to allow for bacterial binding and distal passage of unbound APC. The optimal period can be longer or shorter and is readily determined by measuring the clinical response; for example, response can be determined endoscopically by observation and biopsy.

Step 4 One or more light sources are ingested sequentially and activated in the stomach. The length of time that light is administered by these sources and the number of sources that are ingested will be determined clinically in a light dose escalation study. The churning action of the stomach serves to translocate the light source(s) so that the light is distributed more evenly prior to passage of the source(s) into the duodenum. Since each light source is small (the size of a pill or tablet), it passes easily out through the GI system via peristalsis.

Step 5 The light sources are deactivated after distal passage beyond the gastroduodenal area and excreted in fecal matter.

Note that it is also contemplated that an external light source located over the gastric area can be used to transcutaneously administer light to the treatment site, and that an ultrasonic transducer (not shown here, but generally like that shown in FIG. 5) can alternatively be employed to activate the APC, provided that photosensitizer agent 132 comprising the APC is activated by the frequency of ultrasonic energy transmitted by the transducer. The use of an external light source requires that the APC and the light source absorb and emit in the near infrared range, respectively, so that the light will efficiently penetrate the patient's skin and reach the treatment site. Examples of long waveband photosensitizers are ICG, toluidine blue, and methylene blue, as disclosed herein.

Example 5

Transcutaneous PDT for Targeting Pulmonary Tuberculosis

An APC is formulated to bind with great affinity to *Mycobacterium tuberculosis* in a selective and specific manner. Preferably, the APC is formulated as an aerosol, which can be easily inhaled, enabling distribution into all lung segments. Steam is then inhaled to solubilize any unbound APC and facilitate its removal from the lung by exhalation. Alternatively, the APC is formulated as an injectable compound and administered intravenously. Either way, the bound APC is photoactivated by an external light source disposed on the chest and/or back.

Step 1 The APC is inhaled or injected.

Step 2 Time is allowed to elapse to allow binding of the APC with the *Mycobacterium tuberculosis*, followed by steam inhalation to remove any unbound APC (if inhaled). The time required to ensure a therapeutically effective dose of bound APC may be routinely determined clinically using standard clinical practices and procedures.

Step 3 The light source is disposed adjacent to the thorax and activated for a sufficient time to ensure that therapeutic irradiation has occurred, which may be routinely determined clinically using conventional clinical practices and procedures. The fluence rate and total fluence dose may be determined as noted above. Further, this Example provides helpful guidance for a noninvasive or minimally invasive method using PDT. This is a transcutaneous method of treatment because no incision is required and the subject body is intact. Instead, the light source is introduced into a naturally formed passage of the subject.

Note that alternatively, an internal light source disposed within the thoracic area can be used to administer the light. A further alternative would be the use of an external ultrasonic transducer to produce ultrasonic sound waves that activate the APC. The use of an external light source requires that the APC and the light source respectively absorb and emit light in the near infrared to infrared range to ensure efficient skin penetration of the light. Examples of long waveband photosensitizers are ICG, toluidine blue, methylene blue.

Example 6

Transcutaneous PDT for Targeting Otitis Media

A photosensitizer conjugate is formulated which binds with great affinity to *Streptococcus pneumoniae* and *Hemophilus influenzae* in a selective manner. The APC is formulated into an injectable compound, which can be administered intravenously or instilled topically into the middle ear via a previously placed tympanostomy tube. The drug is activated using light emitted by a small light source about the size, shape, and weight of a hearing aid, which is disposed behind the ear and aimed at the middle ear, so that the light passes into the middle ear transcutaneously.

Step 1 The APC fluid formulation is instilled into the middle ear.

Step 2 Sufficient time is allowed to elapse to allow binding of the APC with the disease organisms, and then, any excess fluid is drained away by gravity or actively aspirated using a needle and syringe.

Step 3 The light source is positioned behind the ear and activated. The light source need not be very intense since the middle ear cavity is very small. Further, the fluence rate and total fluence dose may be followed as discussed above.

Example 7

Transcutaneous PDT for Targeting Antibiotic Associated Pseudomembranous Colitis In cases where *Clostridium difficile* causes pseudomembranous colitis, the same scheme disclosed above for the treatment of *H. pylori* may be applied. The difference is that the APC is targeted toward *C. difficile* and the ingested light source is activated in the colon rather than in the stomach. Alternatively, the photosensitive agent can be activated with transcutaneously transmitted light from an external light source, or by ultrasonic energy produced by an ultrasonic transmitter.

Example 8

Transcutaneous PDT for Targeting Septic Shock Disease

A number of anti-endotoxin antibodies and peptides have been developed and synthesized that can be linked to photosensitizers to form anti-endotoxin APCs. These APCs are injected, allowed to bind and then activated transcutaneously with light, or by using the intracorporeal light emitting devices disclosed in U.S. Pat. No. 5,702,432. For transcutaneous activation, and external light source is placed over a major vessel, preferably an artery, but most preferably a vein where the blood flow is slower, to allow more time for APC activation.

Example 9

Liver Cancer Photodynamic Therapy by Transillumination

Figure 9:
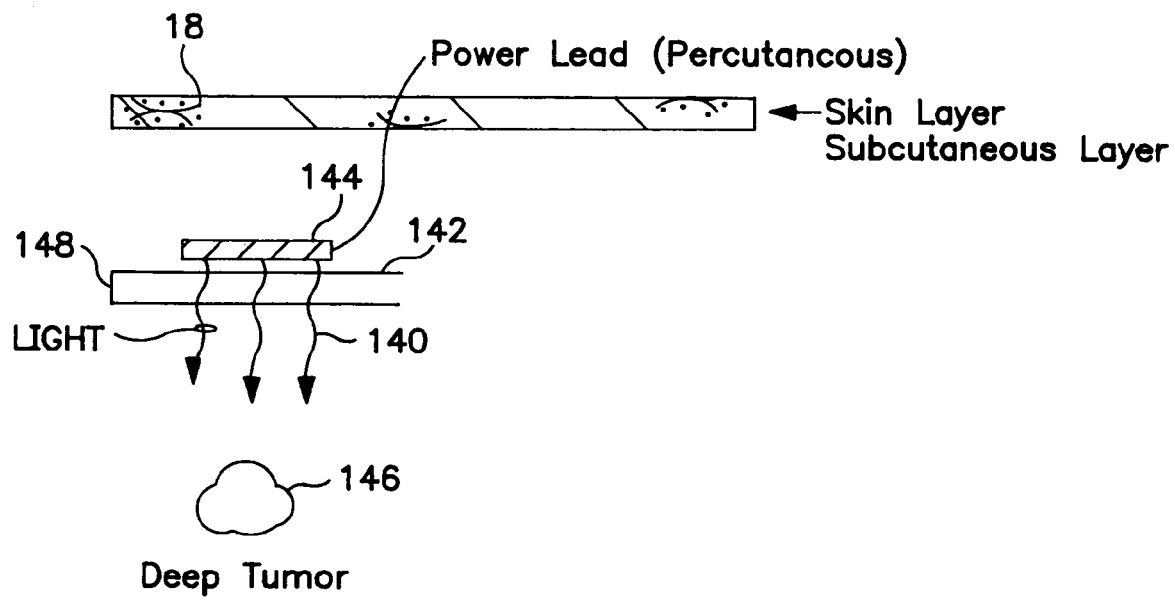
FIG. 9 is a schematic diagram showing how an internal light source administers transillumination of a deep tumor through an organ wall to provide targeted PDT that destroys the tumor.

This Example uses the present invention for the treatment of an organ infiltrated with tumor tissue. Reference is made to FIG. 9. Specifically, light 140 is administered by transillumination through liver tissue 148 from an implanted light source 144 that is disposed external to the surface of liver 142, but within the patient's body underneath the skin layer (18). In this embodiment, a patient is injected intravenously with a photosensitizer agent ICG, conjugated to an antibody that is specific to vascular endothelial antigen (not separately shown) on a tumor 146, so that the antibody binds with the antigen, but not to other tissue in the liver. The optimal dose of ICG will be empirically determined, for example, via a dose escalation clinical trial as is so often performed to evaluate chemotherapeutic agents. One or more light source probes 144 are surgically implanted (e.g., endoscopically) adjacent to, but not invading parenchymal tissue 148 of liver 142. After delaying a time sufficient to permit clearing of the photosensitizer conjugate from the non-target tissues, the light source(s) is(are) activated, irradiating the target tissue with light 140 at a relatively low fluence rate, but administering a high total fluence dose of light in the waveband from about 750 nm to about 850 nm.

The specific dose of photosensitizer conjugate administered to the patient is that which will result in a concentration of active ICG in the blood of between about 0.01 μg/ml and about 100 μg/ml and more preferably, between about 0.01 μg/ml and about 10 μg/ml. It is well within the skill of the ordinary skilled artisan to determine the specific therapeutically effective dose using standard clinical practices and procedures. Similarly, a specific acceptable fluence rate and a total fluence dose may be empirically determined based upon the information provided in this disclosure.

Example 10

Rapid Tissue Clearance and Prolonged Tumor Retention Followed by Transcutaneous Photodynamic Therapy The present example employs Lutrin™ (lutetium texaphyrin, brand: Pharmacyclics, Inc, Sunnyvale, Calif.) as a photosensitizer drug compound. A proportion of Lutrin™ 150 begins to clear from normal tissue 144 in about 3 hours, a larger proportion clears from normal tissue in about 8 hours, with an even greater proportion clearing in about 16 hours. The predominant amount of photosensitizer clears from normal tissue in about 24 hours from administration of the agent. However, tumor tissue 146 retains the photosensitizer up to 48 to 96 hours after administration.

Figure 10A:
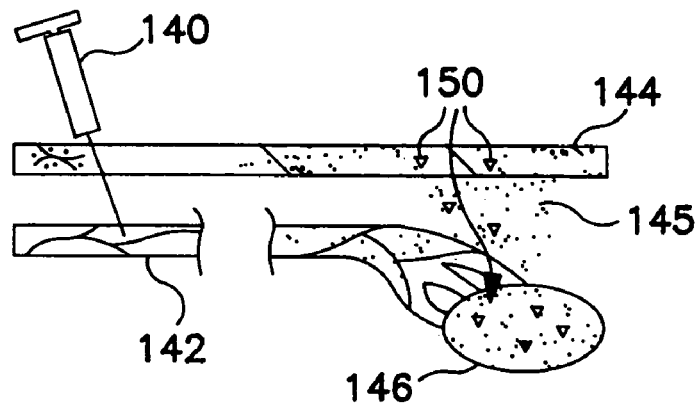
FIGS. 10A–10C are schematic diagrams illustrating the injection of a photosensitizer compound into a vein (FIG. 10A) showing drug clearance from normal tissue after 24 hours and drug retention in tumor beyond 24 hours (FIG. 10B), and showing transcutaneous illumination of the tumor (FIG. 10C)
Figure 10B:
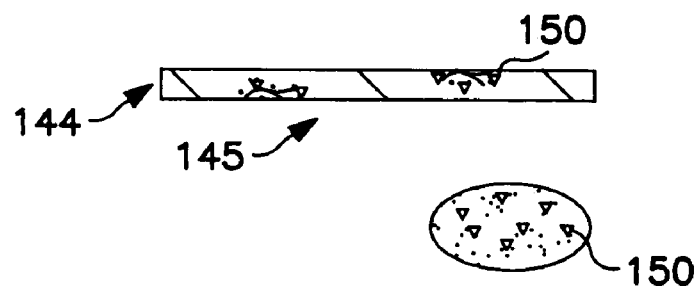
Figure 10C:
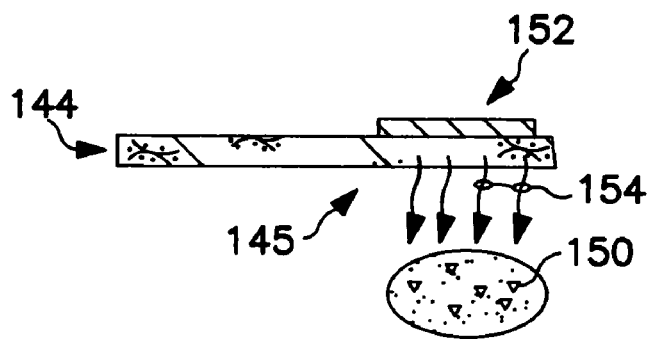
Figure 11:
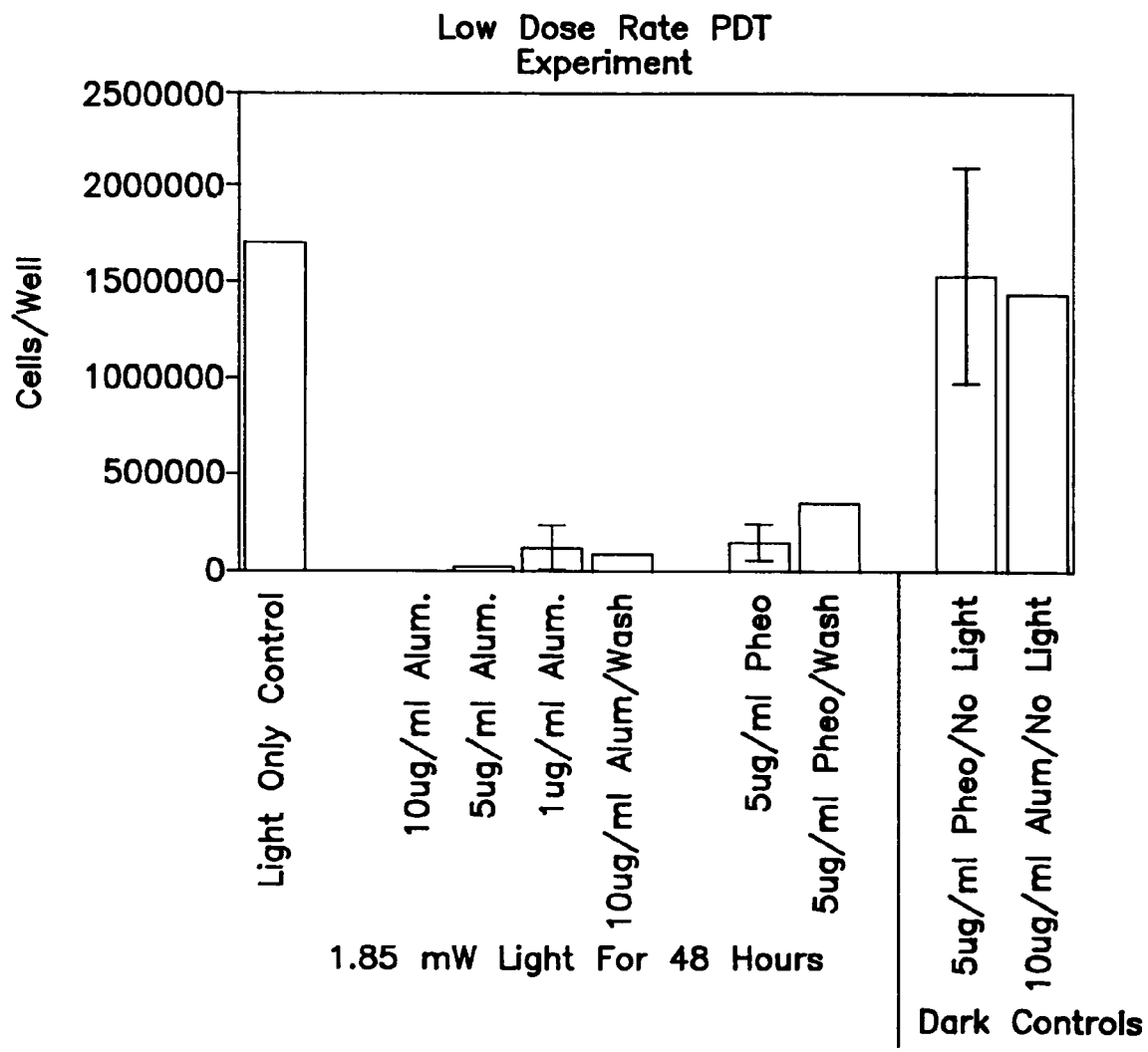
FIG. 11 shows a low dose rate PDT experiment.
Figure 12:
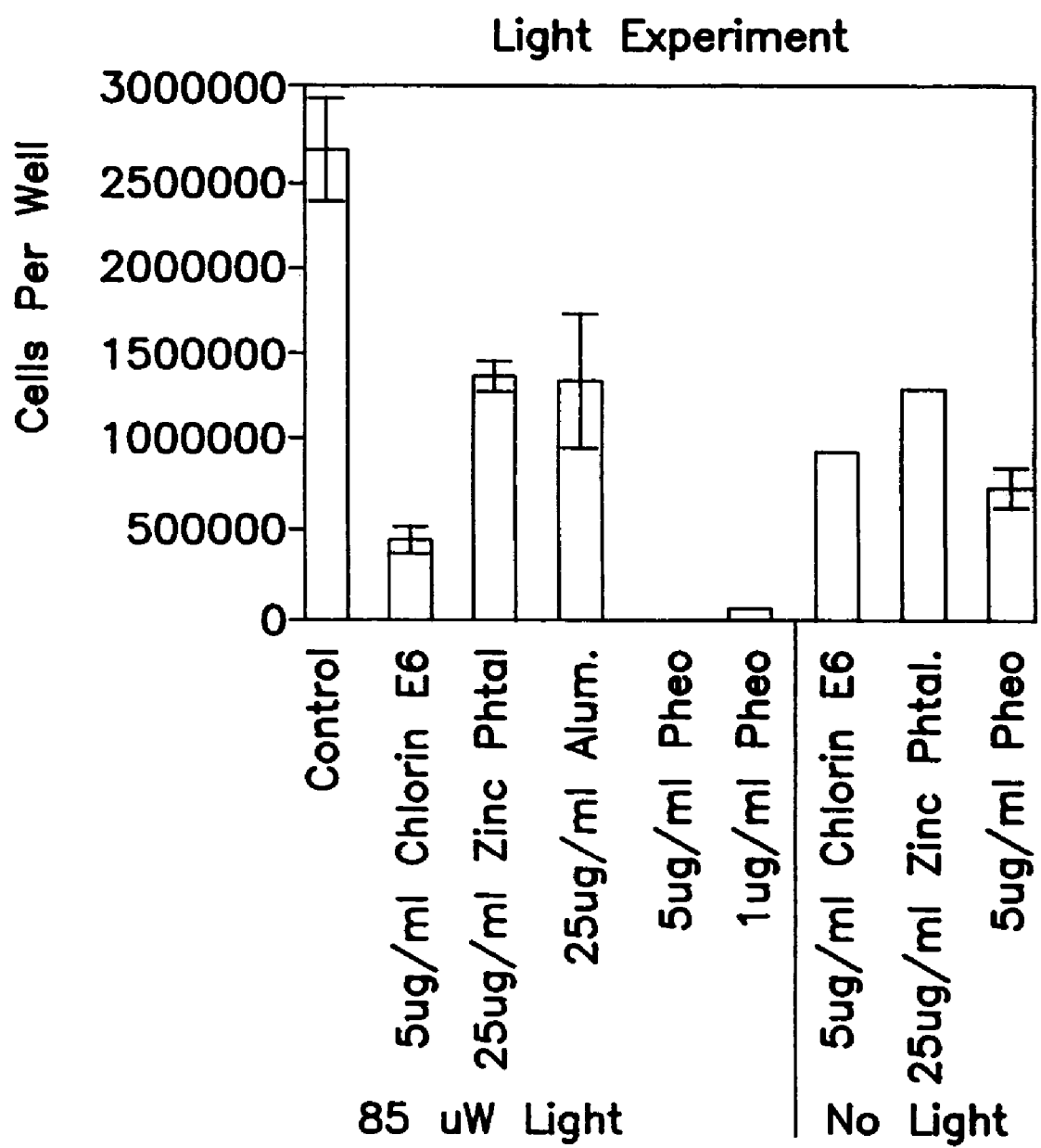
FIG. 12 demonstrates PDT on test cells using several photosensitizer agents.
Figure 13:
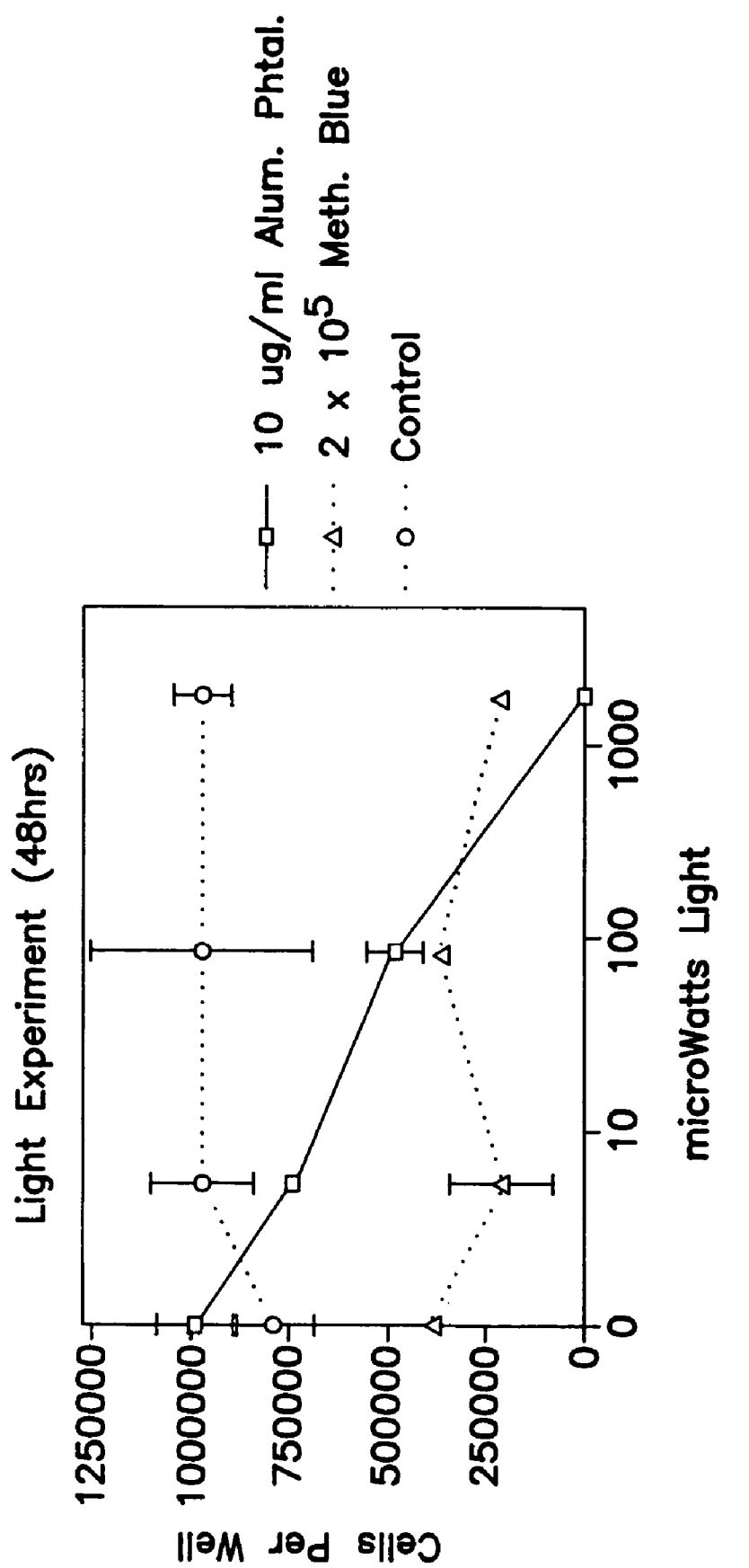
FIG. 13 provides an experiment comparing varying fluence rates of PDT upon test cells.
Figure 14:
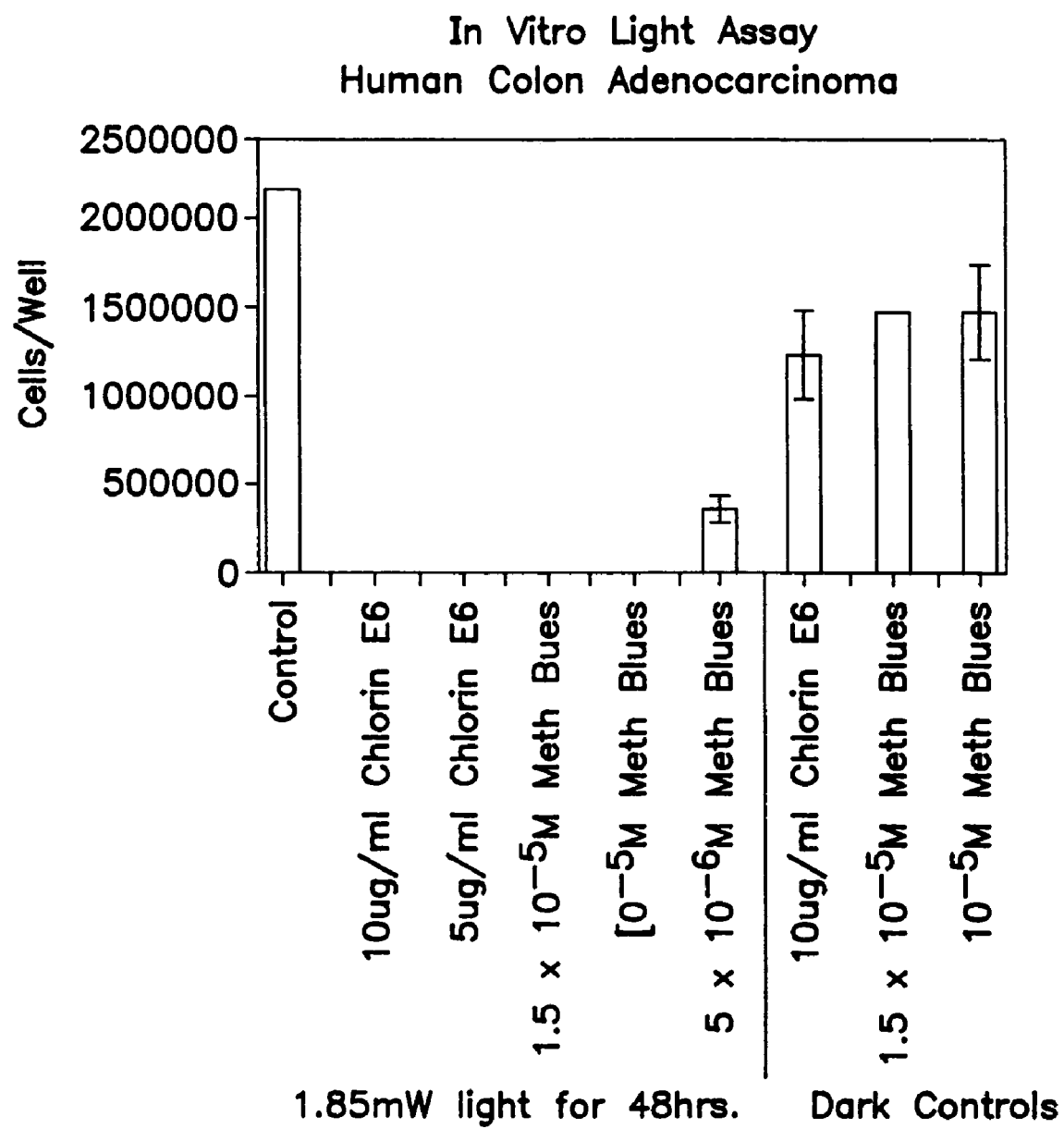
FIG. 14 shows an in vitro PDT assay of human colon adenocarcinoma.

Reference is made to FIGS. 10A–10C. Lutrin™ is administered intravenously 142 by syringe 140 in a clinically determined dosage between 0.05 to 4.0 mg/kg as shown in FIG. 10A. The optimal dosage may be adjusted or determined using standard clinical practice and procedures. Following a period of about 24 hours from administration, the Lutrin™ is cleared from normal tissues including skin 144, and subcutaneous tissues 145. At this point, the Lutrin™ 150 is retained for the most part only in the tumor tissues 146.

An energy source 152, such as a light source, including: an LED array; a laser diode array or any other electroluminescent device, further including a light emitting flat panel, flexible or non-flexible is positioned extracutaneously above the site to be treated. The energy source, such as the LED, is energized and the light 154 is transmitted noninvasively through the skin and intervening tissues to the treatment site. A treatment time of longer than one hour is sustained to insure an adequate number of photochemical reactions completely destroy the target tumor tissues.

The process can be repeated if necessary. Unlike radiotherapy or chemotherapy, there is less significant limitations on the dosage of the photosensitizer or light energy than there is concerning the total dose radiation or chemotherapeutic agent. Radiation and chemotherapy usually result in significant collateral damage to normal tissues and other organ systems. However, since the photosensitizer agent is rapidly cleared from normal tissues, only the tumor tissue is destroyed.

Additionally, the quantum mechanics of transcutaneous photodynamic therapy result in an amplification of the photosensitizer agent. Since each molecule of the photosensitizer agent is repeatedly activated upon transcutaneous illumination, a relatively low dose of the photosensitizer agent can be highly effective in destroying tumor tissue. Whether through singlet oxygen production upon photoactivation or stimulation of an immune response or both, transcutaneous photodynamic therapy demonstrates less adverse reaction or collateral normal tissue damage than most other forms of cancer therapy.

Example 11

PDT of Human Gall Bladder Carcinoma Cells—In Vitro

Human gall bladder carcinoma cells are grown to confluence in 12-well plates. An array of light emitting diodes are suspended above the plates to provide illumination. The cells are loaded with a variety of photosensitizers and illuminated for prolonged periods of time ranging from 48–72 hours with only 30–85 microwatts (μW) of light in some cases. In all cases virtually all tumor cells are reliably killed and histologically exhibit irreversible changes leading to cell death. (See FIGS. 11–14)

Example 12

PDT of Human Gall Bladder Carcinoma Cells—In Vivo

A series of experiments were performed using nude mice growing transplanted human tumors. The mice are injected with various photosensitizers and the tumors illuminated with low fluence of only 30 μW of light over a 72 hour time period. Extended tumor necrosis was observed.

Control

All control nude mice were injected with the PDT drug (intratumor or intraperitoneal) and 5 million human carcinoma cells which developed a tumor mass. These mice were kept in a darkened environment.

Pheophorbide A Experiment

Two experimental mice were injected with epithelial cancer cells preincubated with 10 micrograms of Pheophorbide A. These mice were exposed to 660 nm (peak) light for about 48 hours (30 microwatts per $cm^2$) with no tumor growth after 1.5 months. The control animals ("dark controls") maintained in the absence of light developed a large tumor. Another two mice with established tumors were injected with 50–100 micrograms of Pheophorbide A into the lesion and exposed to 660 nm light (30 microwatts per cm$^2$) for 72 hours. Extensive tumor necrosis resulted after 7 days, but no effect was observed in the dark control animals.

Chlorin e6 Experiment

Two experimental mice were injected with epithelial cancer cells preincubated with 20 micrograms of Chlorin e6. These mice were exposed to 660 nm light for about 48 hours (30 microwatts per cm$^2$) with no tumor growth after 1.5 months. The dark control developed a large tumor. Another two mice were injected with 100–150 micrograms of Chlorin e6 intratumorally and then exposed to 660 nm light (30 microwatts per cm$^2$) for 72 hours. Extensive tumor necrosis resulted in both after 7 days.

Hpd Experiment

Five experimental mice bearing established tumors were injected with 1 mg Hpd intraperitoneally followed by exposure to 630 nm (peak) light (30 microwatts per cm$^2$) for 72 hours. Extensive tumor necrosis was seen upon gross and histological examination in all cases after 7 days. There was no effect observed on control animals maintained in the absence of light (dark control mice).

Conclusion

Exceeding the photodynamic threshold using extended low light level PDT is tumoricidal.

Example 13

PDT of Lesions in a Blood Vessel

Figure 15:
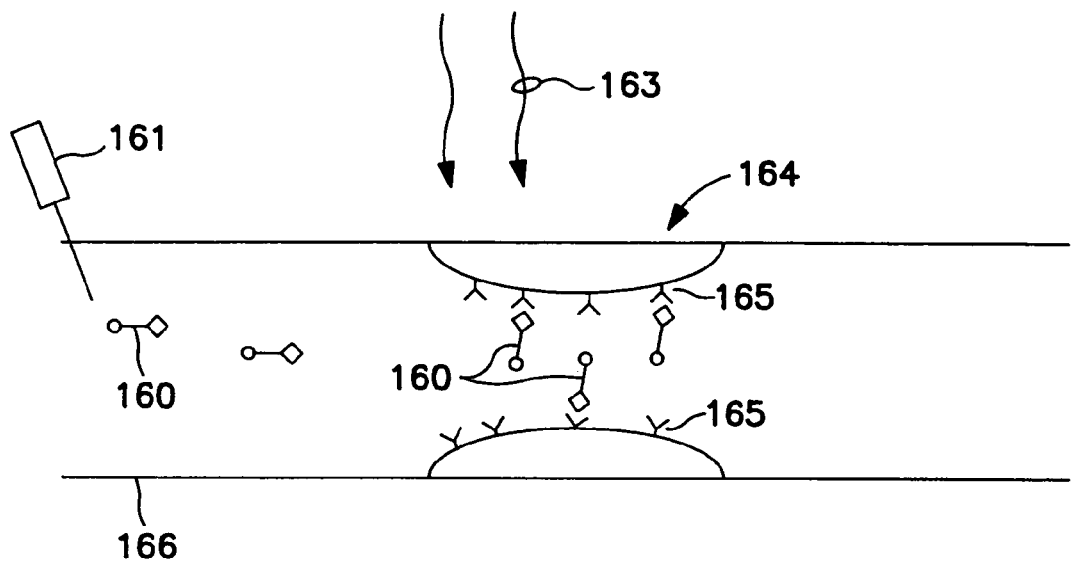
FIG. 15 shows a diagram that demonstrates interstitial transillumination PDT of atherosclerotic plaque in a blood vessel using a photosensitizing agent bound to a ligand specific for receptors or antigens of plaque.
Figure 16:
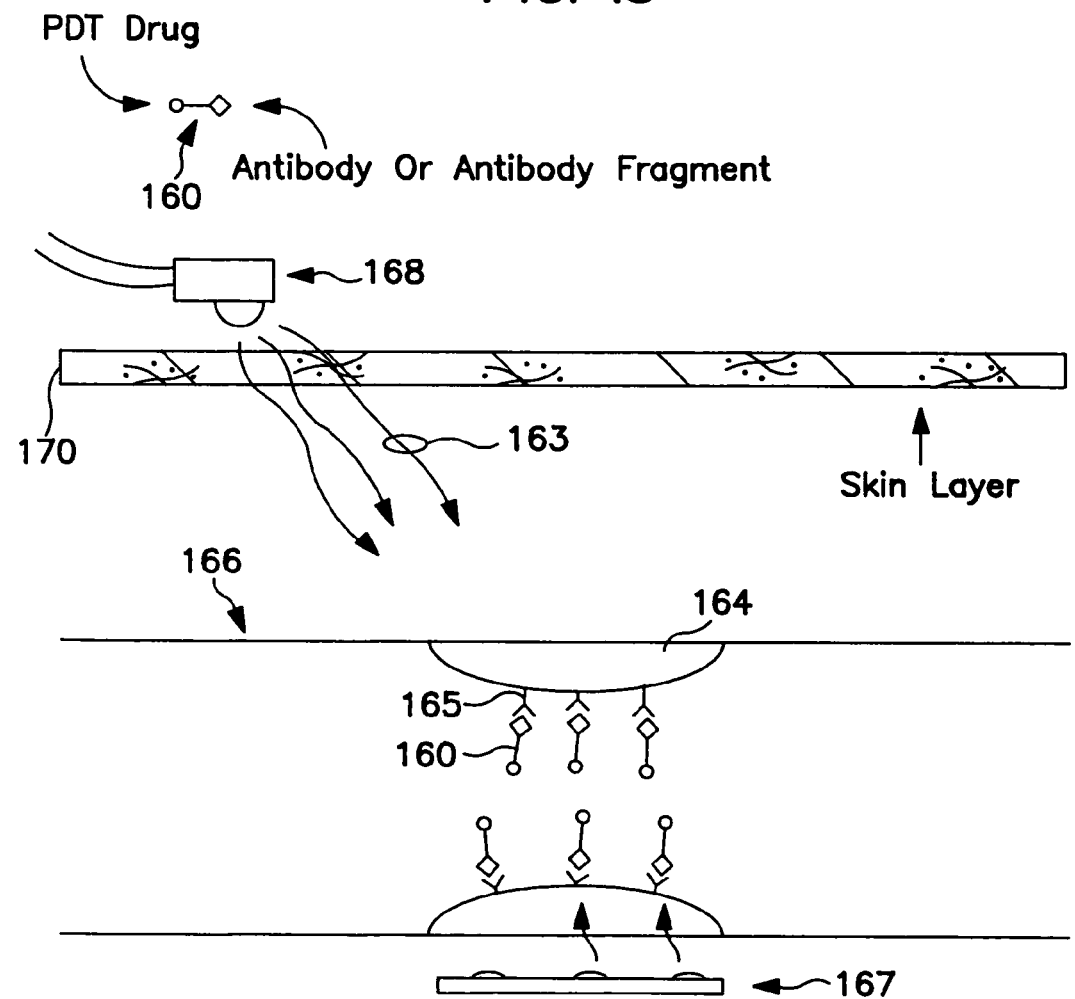
FIG. 16 shows a diagram that demonstrates both transcutaneous PDT and interstitial transillumination PDT of atherosclerotic plaque in a blood vessel using a photosensitizing agent bound to a ligand specific for receptors or antigens of plaque.
Figure 18:
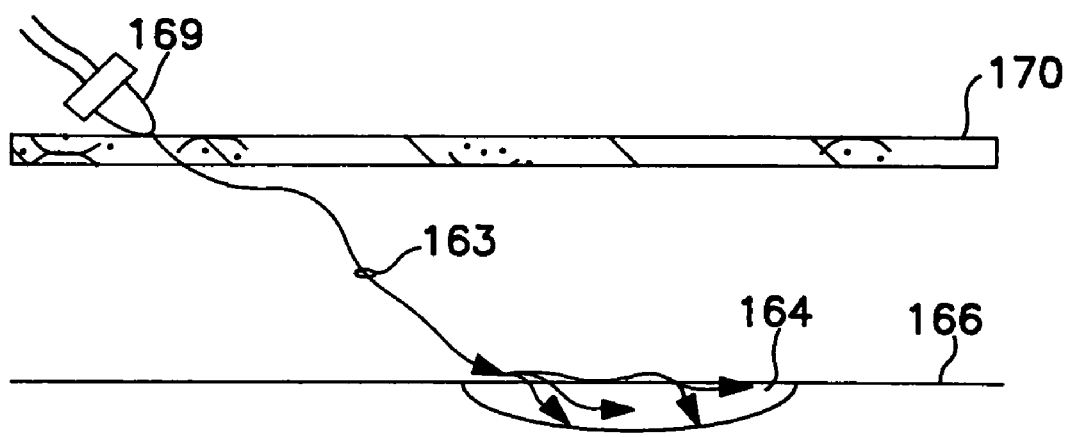
FIG. 18 shows transcutaneous PDT using an optical diffuser attached to an optical fiber with delivery of light from a laser diode light source for the treatment of atherosclerotic plaque in a blood vessel.

A targeted antibody-photosensitizer conjugate (APC) 160 is prepared using an antibody raised against antigens present on a lesion 164, where the lesion is of a type selected from the group consisting of atherosclerotic lesions, arteriovenous malformations, aneurysms, and venous lesions. Alternatively, a ligand-photosensitizer conjugate is prepared using a ligand that binds to a receptor protein 165 present on a lesion.

Where antibody is raised against antigens of atherosclerotic plaque 164, the antibody is bound to a photosensitizing agent, such as ALA forming APCs. APCs 160 are injected intravenously through the skin 170 into the vessel 166 using a hypodermis syringe 161 and allowed to bind and then activated transcutaneously with light 163, or by using the intracorporeal light emitting devices disclosed in U.S. Pat. No. 5,702,432. For transcutaneous activation, an external light source, such as a laser diode 169, is placed over a major vessel 166, preferably an artery, but most preferably a vein where the blood flow is slower, to allow more time for APC activation. (See FIGS. 15, 16 and 18)

Figure 17:
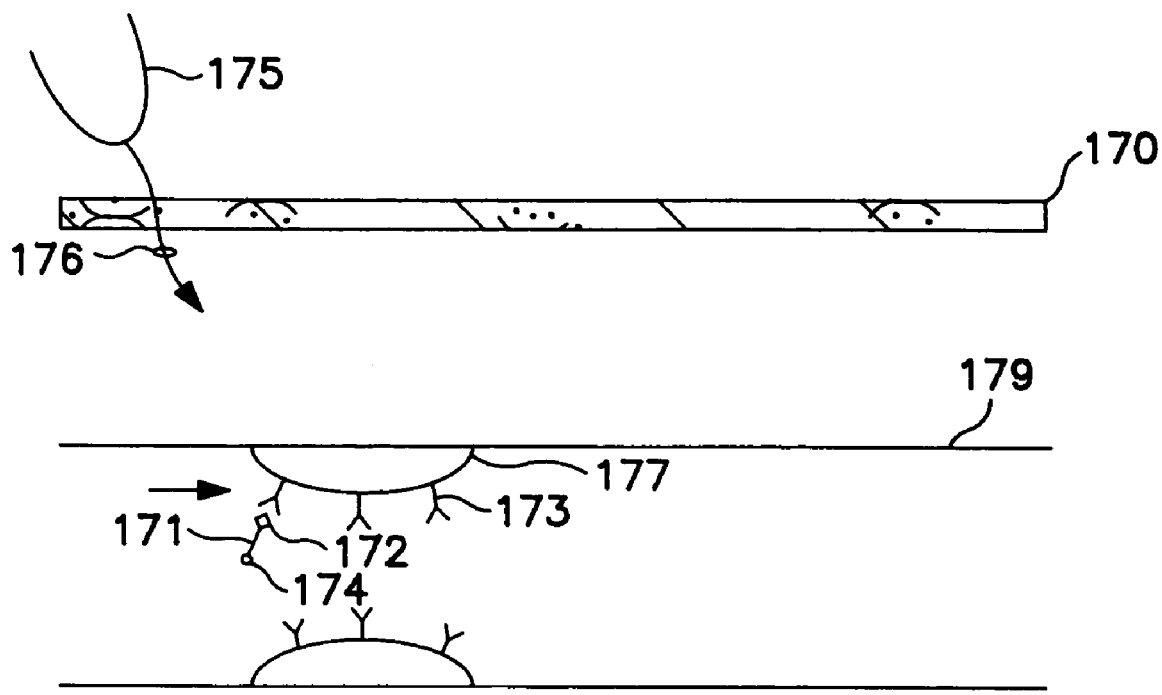
FIG. 17 shows a diagram that demonstrates transcutaneous ultrasound irradiation of atherosclerotic plaque in a blood vessel using an ultrasound energy activated agent bound to a ligand specific for receptors or antigens of plaque.

A variation of this method provides for the preparation of a conjugate 171 of a vessel wall 179 lesion 177 specific protein 173 or ligand 172 to a sonic energy 176 activated compound 174 and irradiated transcutaneously using and ultrasound probe 175 external to the skin 170. (See FIG. 17)

This invention has been described by a direct description and by examples. As noted above, the examples are meant to be only examples and not to limit the invention in any meaningful way. Additionally, one having ordinary skill in the art to which this invention pertains in reviewing the specification and claims which follow would appreciate that there are equivalents to those claimed aspects of the invention. The inventors intend to encompass those equivalents within the reasonable scope of the claimed invention.

What is claimed is:

1. A method for administering a photodynamic therapy to destroy or impair target cells expressing a VEGF receptor in a mammalian subject, comprising the steps of:
   (a) administering to the mammalian subject a therapeutically effective amount of a liposome delivery system, comprising:
      (i) a first conjugate comprising a first member of a ligand-receptor binding pair conjugated to one of an antibody and an antibody fragment that selectively binds to a VEGF receptor of the target cells;
      (ii) a second conjugate comprising a second member of the ligand-receptor binding pair, conjugated to a photoreactive compound; and
      (iii) a liposome, separately conjugated to the second member of the ligand-receptor binding pair, wherein:
   the first member binds to the second member of the ligand-receptor binding pair;
   (b) irradiating at least a portion of the mammalian subject in which the target cells are disposed, using light having a waveband corresponding at least in part to the characteristic light absorption waveband of the photoreactive compound; wherein
      the intensity of the light used for the step of irradiating and the duration of irradiation have been selected such that the target cells are destroyed and the non-target tissue through which the light passes remains undamaged.

2. The method of claim 1, further comprising the step of allowing sufficient time for any targeted photosensitizer compound that is not bound to the target cells to clear from the non-target cells of the mammalian subject prior to the step of irradiating.

3. The method of claim 1, wherein the target cells are comprised in a target tissue selected from the group consisting of a vascular endothelial tissue, an abnormal vascular wall of a tumor, a solid tumor, a tumor of head, a tumor of a neck, a tumor of a gastrointestinal tract, a tumor of a liver, a tumor of a breast, a tumor of a prostate, a tumor of a lung, a nonsolid tumor, malignant cells of one of a hematopoietic tissue and a lymphoid tissue, lesions in a vascular system, a diseased bone marrow, and diseased cells in which the disease is one of an autoimmune and an inflammatory disease.

4. The method of claim 3, wherein the target tissue is a lesion of a type selected from the group consisting of atherosclerotic lesions, arteriovenous malformations, aneurysms, and venous lesions.

5. The method of claim 1, wherein the step of irradiating comprises the step of providing a light source that is disposed internal to an intact skin layer of the mammalian subject and wherein said light source is activated to produce the light.

6. The method of claim 1, wherein the step of irradiating comprises providing a light source that is disposed external to an intact skin layer of the mammalian subject and wherein the light source is activated to produce the light.

7. The method of claim 1, wherein the photoreactive compound is selected from the group consisting of indocyanine, methylene blue, toluidine blue, aminolevulinic acid, chlorins, phthalocyanines, porphyrins, purpurins, bacteriochlorins, merocyanines, psoralens and texaphyrins.

8. The method of claim 1, wherein the step of irradiating is carried out for a time interval of from about 4 minutes to about 72 hours.

9. The method of claim 1, wherein the step of irradiating is carried out for a time interval of from about 60 minutes to about 48 hours.

10. The method of claim 1, wherein the step of irradiating is carried out for a time interval of from about 2 hours to about 24 hours.

11. The method of claim 1, wherein the total fluence of the light used for irradiating is between about 30 Joules and about 25,000 Joules.

12. The method of claim 1, wherein the total fluence of the light used for irradiating is between about 100 Joules and about 20,000 Joules.

13. The method of claim 1, wherein the total fluence of the light used for irradiating is between about 500 Joules and about 10,000 Joules.

14. A method for administering a photodynamic therapy to destroy or impair target cells in a tumor in a mammalian subject, comprising the steps of:
  (a) administering to the subject a therapeutically effective amount of a targeted photosensitizer compound having a characteristic light absorption waveband, wherein:
    the targeted photosensitizer compound selectively binds with the target cells; and
    the photosensitizer compound is targeted to a receptor on a vascular endothelial tissue or an abnormal vascular wall of a tumor;
  (b) activating the photosensitizer bound to the target cells by irradiating with light having a waveband corresponding at least in part to the characteristic light absorption waveband of the targeted photosensitizer compound from a light source disposed within the tumor, wherein:
    the intensity of the light used for the step of irradiating and the duration of irradiation are selected such that within a zone of treatment the target cells are destroyed and the non-target tissue through which the light passes remains undamaged; and
  (c) sequentially expanding the zone of treatment outward in a stepwise manner by repositioning the light source, thereby destroying tumor tissue.

15. The method of claim 14, wherein the receptor is a VEGF receptor.

16. The method of claim 14, further comprising the step of allowing sufficient time for any targeted photosensitizer compound that is not bound to the target cells to clear from the non-target cells of the mammalian subject prior to the step of irradiating.

17. A liposome delivery system, comprising:
  (i) a first conjugate comprising a first member of a ligand-receptor binding pair conjugated to one of an antibody and an antibody fragment that selectively binds to a VEGF receptor of the target cells;
  (ii) a second conjugate comprising a second member of the ligand-receptor binding pair, conjugated to a photoreactive compound; and
  (iii) a liposome, separately conjugated to the second member of the ligand-receptor binding pair, wherein the first member binds to the second member of the ligand-receptor binding pair.

* * * * *